United States Patent
Shekhar et al.

(10) Patent No.: US 10,251,562 B2
(45) Date of Patent: Apr. 9, 2019

(54) APPARATUS AND METHOD FOR DETECTING HEART MURMURS

(71) Applicant: Children's National Medical Center, Washington, DC (US)

(72) Inventors: Raj Shekhar, Dayton, MD (US); Robin Doroshow, Bethesda, MD (US); Sukryool Kang, Arlington, VA (US); James McConnaughey, Washington, DC (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 456 days.

(21) Appl. No.: 14/990,693

(22) Filed: Jan. 7, 2016

(65) Prior Publication Data

US 2016/0192846 A1 Jul. 7, 2016

Related U.S. Application Data

(60) Provisional application No. 62/100,698, filed on Jan. 7, 2015.

(51) Int. Cl.
*A61B 5/02* (2006.01)
*A61B 7/02* (2006.01)
(Continued)

(52) U.S. Cl.
CPC .......... *A61B 5/02028* (2013.01); *A61B 7/02* (2013.01); *A61B 7/04* (2013.01); *A61B 5/7267* (2013.01);
(Continued)

(58) Field of Classification Search
CPC ..... A61B 5/02028; A61B 5/7267; A61B 7/02; A61B 7/04; A61B 2562/0204; A61B 2562/225
(Continued)

(56) References Cited

U.S. PATENT DOCUMENTS

| 5,010,889 A | 4/1991 | Bredesen et al. |
| 7,001,338 B2 | 2/2006 | Hayek et al. |

(Continued)

FOREIGN PATENT DOCUMENTS

| WO | WO 00/02486 A1 | 1/2000 | |
| WO | WO 0002486 A1 * | 1/2000 | ............... A61B 7/04 |
| WO | 2015/005850 A1 | 1/2015 | |

OTHER PUBLICATIONS

International Search Report and Written Opinion dated Jul. 26, 2016 in PCT/US 16/12528.
(Continued)

*Primary Examiner* — Michael Carey
(74) *Attorney, Agent, or Firm* — Oblon, McClelland, Maier & Neustadt, L.L.P.

(57) ABSTRACT

Discussed herein are an apparatus and a corresponding method for classifying a murmur detected in a heart signal as a Still's murmur. Circuitry included in the apparatus segments a heart signal to detect a first lobe (S1) and a second lobe (S2) of the heart signal. Further, the circuitry computes a spectral width of an extracted feature of the heart signal that lies in a portion of a time interval between the S1 lobe and the S2 lobe based on an estimated power spectral density. Additionally, a peak frequency of the extracted feature of the heart signal and a shape of an envelope of the extracted feature of the heart signal are computed. The extracted feature of the heart signal is classified as the Still's murmur based on the spectral width, the peak frequency, the shape of the envelop, and additional murmur discriminant features.

8 Claims, 14 Drawing Sheets

(51) Int. Cl.
*A61B 7/04* (2006.01)
*A61B 5/00* (2006.01)

(52) U.S. Cl.
CPC . *A61B 2562/0204* (2013.01); *A61B 2562/225* (2013.01)

(58) Field of Classification Search
USPC .................................................. 600/508, 528
See application file for complete search history.

(56) References Cited

U.S. PATENT DOCUMENTS

| | | | |
|---|---|---|---|
| 8,992,435 | B2 | 3/2015 | Pretorius et al. |
| 2004/0076303 | A1 | 4/2004 | Vyshedskly et al. |
| 2006/0142667 | A1 | 6/2006 | Munk |
| 2006/0161064 | A1 | 7/2006 | Watrous et al. |
| 2008/0013747 | A1 | 1/2008 | Tran |
| 2010/0145210 | A1 | 6/2010 | Graff et al. |
| 2010/0160807 | A1 | 6/2010 | Schmidt et al. |
| 2011/0096936 | A1* | 4/2011 | Gass ........................ A61B 7/04 381/67 |
| 2013/0226019 | A1 | 8/2013 | Pretorius et al. |
| 2014/0107515 | A1 | 4/2014 | Lee et al. |
| 2014/0163422 | A1* | 6/2014 | Poplaw ................. H04M 1/026 600/586 |
| 2015/0164466 | A1 | 6/2015 | Pretorius et al. |

OTHER PUBLICATIONS

European Search Report dated Jul. 11, 2018 in Patent Application No. 16735428.1.
W.R. Thompson, et al., "Automated Cardiac Auscultation for Detection of Pathologic Heart Murmurs", Pediatric Cardiology, vol. 22, No. 5, XP055488671, 2001, 7 pages.
Extended European Search Report dated Oct. 16, 2018 in Patent Application No. 16735428.1.

* cited by examiner

APPARATUS AND METHOD FOR DETECTING HEART MURMURS

INCORPORATION BY REFERENCE

The present disclosure claims the benefit of U.S. Provisional Application No. 62/100,698, filed on Jan. 7, 2015, which is incorporated herein by reference in its entirety.

FIELD

The present disclosure relates generally to the field of auscultation, which is a process of listening to the heart, lungs, and gastrointestinal systems in order to assess their functions and detect diseases. Specifically, the present disclosure relates to an apparatus and methods thereof for detecting Still's murmur.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Each year numerous children are referred by their pediatricians or primary care physicians to a cardiologist for further consultation upon detection of a heart murmur. A heart murmur is a sound occurring during a regular heartbeat cycle that is caused by turbulent blood in or near the heart area. However, a majority of the referrals are diagnosed as Still's murmur (an innocent heart murmur that occurs in childhood).

Still's murmur is a normal finding present in approximately 50-90% of healthy children. Still's murmur is most often present throughout the preschool and elementary-school years of a child, but may also be present in infants and older children. The incidence of Still's murmur exceeds the incidence of actual congenital heart defects (pathological murmurs) by over 50-fold. Still's murmur is characterized by a low-pitched pure tone that exists for a short duration between heart sounds and does not require any treatment. Furthermore, the occurrences of Still's murmur usually resolve by young adulthood.

However, the inability of primary care physicians (e.g., pediatricians) to distinguish between Still's murmur and a pathological murmur leads to a substantial number of specialist consultations and cardiac tests. The consultations and cardiac tests result in a high cost to the healthcare system and causes unnecessary anxiety for the patients and their parents. Furthermore, multiple studies have demonstrated that only cardiologists, among medical caregivers, can reliably make a distinction between pathological heart murmurs and Still's murmurs by using only a stethoscope, and that this skill does not improve in other medical caregivers with experience. Therefore, if the primary care physician (or other medical professional) detects a heart murmur that may indeed be a Still's murmur, he or she is most likely to refer the patient to a specialist for consultation and/or further testing, as the physician is unable to successfully diagnose the heart murmur as the benign Still's murmur.

Accordingly, there is a requirement for an apparatus and a technique for detecting Still's murmur in an efficient and reliable manner, such that unnecessary referrals of children with normal hearts to specialists are prevented.

SUMMARY

The present disclosure provides for an apparatus and corresponding methods for determining a type of heart murmur. Specifically, the disclosure provides for a mobile device based solution that enables primary care physicians, such as pediatricians, to successfully identify Still's murmur.

Accordingly, an aspect of the present disclosure provides for a system comprising: a device including an input port configured to receive a heart signal from a stethoscope; a connector that connects the device to the stethoscope and configured to relay the heart signal from the stethoscope to the device; and circuitry configured to classify an extracted feature of the heart signal as a Still's murmur after processing the heart signal.

Further, an aspect of the present disclosure provides that the input port of the device is one of an audio port or a data port, the connector includes a mount that is affixed to the device, an external contour of the mount matches a contour of the device, and the mount includes an attachment that connects to a stethoscope attachment and through which the heart signal is received.

Further, an aspect of the present disclosure provides that the connector includes a microphone attachment, a cable, and a microphone receiver; the microphone attachment connects to the input port of the device; the microphone receiver connects to an input port of the stethoscope; and the cable connects the microphone attachment to the microphone receiver.

Further, an aspect of the present disclosure provides that the connector includes a cable, an attachment, and a microphone receiver; the attachment includes an analog-to-digital converter and a pre-amplifier; the microphone receiver receives an analog heart signal from the stethoscope; the analog-to-digital converter converts the analog heart signal into a digital heart signal; and the cable relays the digital heart signal to the input port of the device.

Further, an aspect of the present disclosure provides that the circuitry is configured to classify the extracted feature of the heart signal as the Still's murmur after processing the heart signal by being configured to segment the heart signal to detect a first lobe (S1) and a second lobe (S2) of the heart signal; compute a spectral width of the extracted feature that lies in a portion of a time interval between the S1 lobe and the S2 lobe based on an estimated power spectral density; compute a peak frequency of the extracted feature of the heart signal; compute a shape of an envelope of the extracted feature of the heart signal; and classify the extracted feature of the heart signal as the Still's murmur based on the spectral width, the peak frequency, the shape of the envelop, and additional murmur discriminant features.

Further, an aspect of the present disclosure provides that the circuitry is configured to classify the extracted feature as the Still's murmur based on whether the spectral width is within a predetermined threshold.

Further, an aspect of the present disclosure provides a device comprising: an input port configured to receive a heart signal; a display configured to display the heart signal, to display a user interface to allow a user to review and edit the heart signal, and to display sound corresponding to the heart signal; and circuitry configured to classify an extracted feature of the heart signal as a Still's murmur after processing the heart signal, wherein the user inputs patient data information via the user interface, and the device further comprising: a memory configured to store the patient data information, the heart signal, the sound corresponding to the heart signal, and the edited heart signal.

Further, an aspect of the present disclosure provides that the circuitry is configured to classify the extracted feature of the heart signal as the Still's murmur after processing the heart signal by being configured to: segment the heart signal to detect a first lobe (S1) and a second lobe (S2) of the heart signal; compute a spectral width of the extracted feature that lies in a portion of a time interval between the S1 lobe and the S2 lobe based on an estimated power spectral density; compute a peak frequency of the extracted feature of the heart signal; compute a shape of an envelope of the extracted feature of the heart signal; and classify the extracted feature of the heart signal as the Still's murmur based on the spectral width, the peak frequency, the shape of the envelop, and additional murmur discriminant features.

Further, an aspect of the present disclosure provides a device comprising circuitry configured to: segment a heart signal to detect a first lobe (S1) and a second lobe (S2) of the heart signal; compute a spectral width of an extracted feature of the heart signal that lies in a portion of a time interval between the S1 lobe and the S2 lobe based on an estimated power spectral density; compute a peak frequency of the extracted feature of the heart signal; compute a shape of an envelope of the extracted feature of the heart signal; and classify the extracted feature of the heart signal as the Still's murmur based on the spectral width, the peak frequency, the shape of the envelop, and additional murmur discriminant features, wherein the circuitry is configured to classify the extracted feature as the Still's murmur based on whether the spectral width is within a predetermined threshold, wherein the circuitry is configured to measure the spectral width at a frequency where a magnitude of the estimated power spectral density of the extracted feature is 20% of a maximum power spectral density of the extracted feature, wherein the circuitry classifies the extracted feature as the Still's murmur based on the shape of the envelope of the extracted feature being a crescendo-decrescendo or diamond shape, wherein the portion of the time interval is located to the right of a detected position of the S1 lobe of the heart signal, the portion being offset from the S1 lobe by an offset amount and having a duration that is smaller than the time interval between the S1 lobe and the S2 lobe, wherein the circuitry is configured to validate the detected S1 lobe and S2 lobe of the heart signal based on widths of the S1 lobe and the S2 lobe being less than a predetermined width and a distance between the S1 lobe and the S2 lobe being above a threshold distance, wherein the threshold distance is 50 milli-seconds and the predetermined width 250 milli-seconds, wherein the circuitry is configured to classify the extracted feature as a non-Still's murmur based on at least one of the extracted feature being located in a region of the heart signal that exceeds the portion of the time interval between the S1 lobe and the S2 lobe, the spectral width being above the predetermined threshold, and the shape of the envelope of the extracted feature not being a crescendo or diamond shape, wherein the circuitry is configured to classify the extracted feature as the Still's murmur or a non-Still's murmur based on a comparison of features of the heart signal to data retrieved from a database, wherein the circuitry is configured to classify the extracted feature as the Still's murmur or a non-Still's murmur based on a machine learning algorithm that is trained using a large database of murmurs with definite clinical diagnosis, and wherein the machine learning algorithm receives computed features corresponding to the heart signal and outputs a type of murmur corresponding to the extracted feature of the heart signal.

The foregoing paragraphs have been provided by way of general introduction, and are not intended to limit the scope of the following claims. The described embodiments together, with further advantages, will be best understood by reference to the following detailed description taken in conjunction with the accompanying drawings.

BRIEF DESCRIPTION OF THE DRAWINGS

Various embodiments of this disclosure that are provided as examples will be described in detail with reference to the following figures, wherein like numerals reference like elements, and wherein.

DETAILED DESCRIPTION

Figure 1:
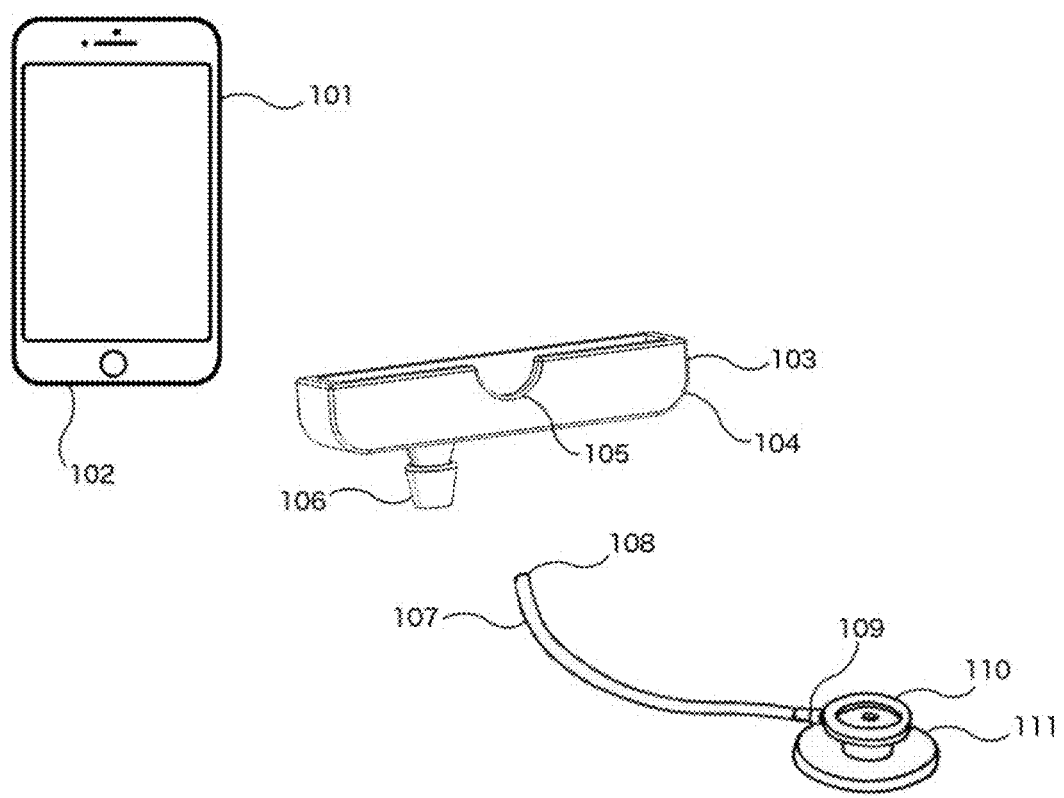
FIG. 1 illustrates, according to an embodiment, a mobile device including a two-part stethoscope attachment.

While other attempted techniques attempt to detect pathological murmurs in an obtained heart signal (which has been shown to be less than 100% effective), the present approach is directed to detecting non-pathological murmurs such as Still's murmur. Such an approach is directed to detecting murmurs which are benign while leaving the detection of pathological murmurs to a referred physician. The present approach saves significant healthcare costs and potential patient stress as it eliminates unnecessary referrals and assists healthcare workers by identifying the non-pathological murmurs, while classifying all other murmurs as potentially pathological. This approach is different from any other past automated approaches and is much safer for the patent as borderline cases can simply be classified as potentially pathological ensuring patient safety.

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and devices provided in particular implementations. However, the processes and devices will operate effectively in other implementations. Phrases such as "an embodiment", "one embodiment" and "another embodiment" may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by appended claims.

Furthermore, where a range of values is provided, it is to be understood that each intervening value between the upper and lower limit of the range—and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

FIG. 1 illustrates, according to an embodiment, an exemplary mobile device 101 including a two-part stethoscope attachment. In FIG. 1, the mobile device 101 has a built-in port 102. The port 102 is located near the bottom of the mobile device 101 close to where a user's mouth would be positioned during a phone conversation. The mobile device 101 attaches to a stethoscope mount 103. The stethoscope mount 103 has an external contour 104 that matches to the contour of the mobile device 101. Thus, the mobile device 101 may be affixed to the stethoscope mount 103.

Further, the stethoscope mount 103 includes a cutout portion 105 that provides a user unhindered access to the mobile device 101. The cutout portion 105 can be of any shape and is not restricted to the shape illustrated in FIG. 1. The stethoscope mount 103 also includes a barbed connector 106 to which a stethoscope attachment (stethoscope tube) 107 may be attached. The stethoscope attachment 107 may be made of a rubber like material that attaches to the barbed connector 106 at an open end 108. At the other end, the stethoscope attachment 107 is attached by a barbed connector 109 to a bell 110 and diaphragm 111 that are used for auscultation purposes.

Figure 2A:
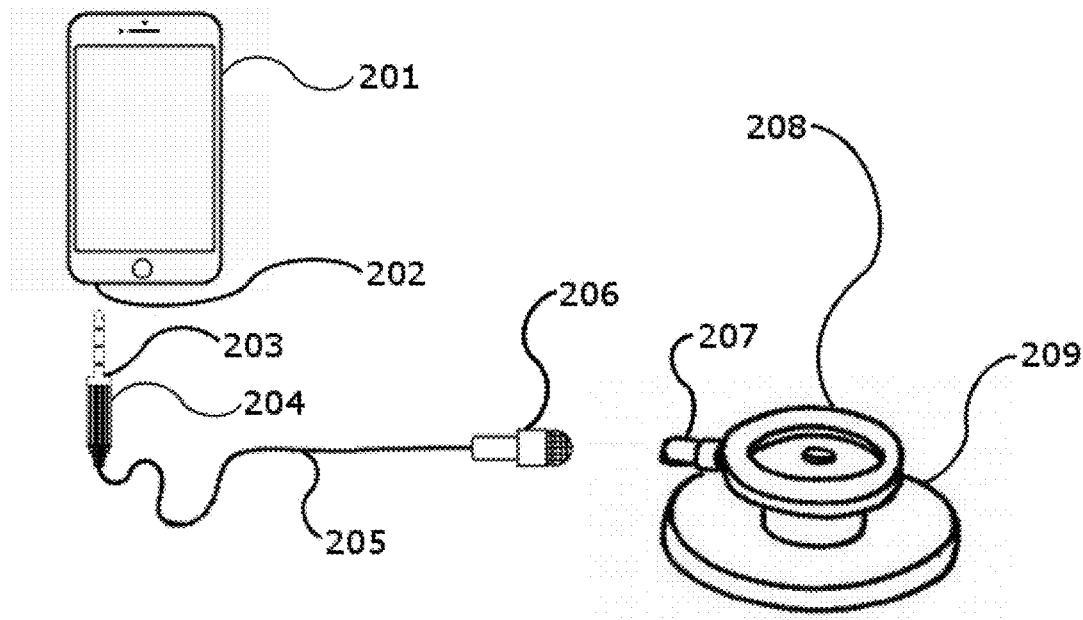
FIG. 2A illustrates, according to an embodiment, a mobile device and a stethoscope attachment.

FIG. 2A illustrates, according to an embodiment, a perspective view depicting an attachment between a mobile device 201 and a stethoscope. In FIG. 2, the mobile device 201 includes an audio port 202 that is disposed at a lower or upper edge of the mobile device 201. The audio port 202 includes an opening where a microphone lead 203 of a microphone attachment 204 may be inserted. The microphone attachment 204 includes a 3.5 mm cable 205 that is attached to a microphone head/receiver 206. Further, the microphone head/receiver 206 is attached to a stethoscope head 207, which has a bell 208 and diaphragm 209 that can be used for auscultation purposes. In such a manner, the stethoscope, as depicted in FIG. 2, makes an electrical connection (via the microphone attachment) to the mobile device 201. The heart sound received from the stethoscope is converted to an electrical signal (using the microphone attachment 204, cable 205, microphone lead 203, and the microphone head/receiver 206) prior to being received by the audio port 202 of the mobile device 201.

Figure 2B:
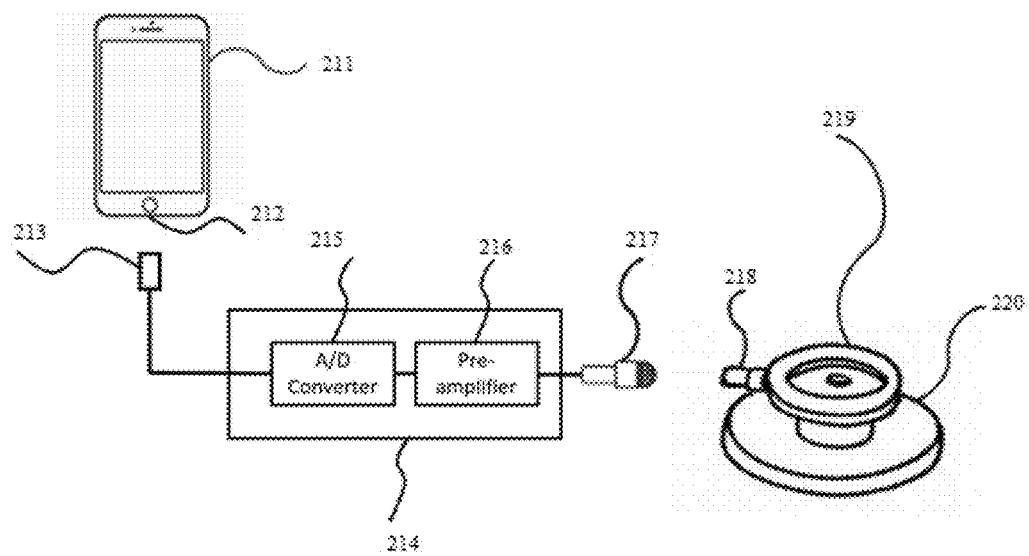
FIG. 2B illustrates, according to an embodiment, a mobile device and another stethoscope attachment.

FIG. 2B illustrates, according to an embodiment, a perspective view depicting an attachment between a mobile device 211 and a stethoscope. In FIG. 2B, the mobile device 211 includes a digital port (for example, Micro-USB for Android™ devices or Lightning® port for Apple® devices) 212 that is disposed at a lower center portion of the mobile device 211. The digital port 212 includes an opening where a Micro-USB or Lighting cable 213 of an attachment 214 may be inserted. The attachment 214 includes A/D converter 215 that is connected to a microphone pre-amplifier 216. The pre-amplifier 216 is connected to the microphone head/receiver 217. Further, the microphone head/receiver 217 is attached to a stethoscope head 218, which has a bell 219 and diaphragm 220 that can be used for auscultation purposes. In such a manner, the stethoscope, as depicted in FIG. 2B, makes an electrical connection (via the attachment 214) to the mobile device 211. Instead of digitizing heart sounds from the analog stethoscope using the mobile device 211, the heart sounds can be digitized using an external device (i.e., an attachment 214). The audio circuit on the mobile devices are optimized for human voice. Digitizing the heart sound using mobile devices may not be able to capture the low frequency components of the heart sound. The attachment 214 (including the AD) converter 215 and pre-amplifier 216) and the microphone head/receiver 217 that can capture the sound from 20 Hz to 1000 Hz are used.

Each of the mobile devices 101, 201, and 211 as shown in FIGS. 1, 2A, and 2B, respectively, may include a processor (circuitry) and sufficient memory having stored therein one or more sets of instructions, e.g., in the form of a user application or 'app', that is executable by the processor, in order to enable a user of the mobile device to successfully detect and distinguish a Still's murmur from a pathological heart murmur. Details regarding the techniques used to detect a Still's murmur are described later with reference to FIG. 9.

Examples of mobile devices 101, 201, and 211 that may be used to detect Still's murmur include, but are not be limited to, smart phones (such as an iPhone), personal communication devices (PDAs), application-specific mobile electronic devices and/or other mobile electronic devices having sufficient memory and computing power to execute a set of instructions that enable a user of the mobile device to successfully detect Still's murmur. Further, the 'app' installed on the mobile device may also be used as a business development tool. For instance, the 'app' may be used to increase profits by leveraging business development tools contained within the 'app' and/or accessed through the 'app'. For example, two areas of business development may be addressed by the app: 1) increasing sales of the device by offering, demonstrating and proving the effectiveness in successfully detecting Still's murmur without professional guidance, and 2) increase operational efficiency, and ease of use of the device by providing a stepwise instruction that directs a user in operating the device, thereby reducing overhead costs.

Figure 3:
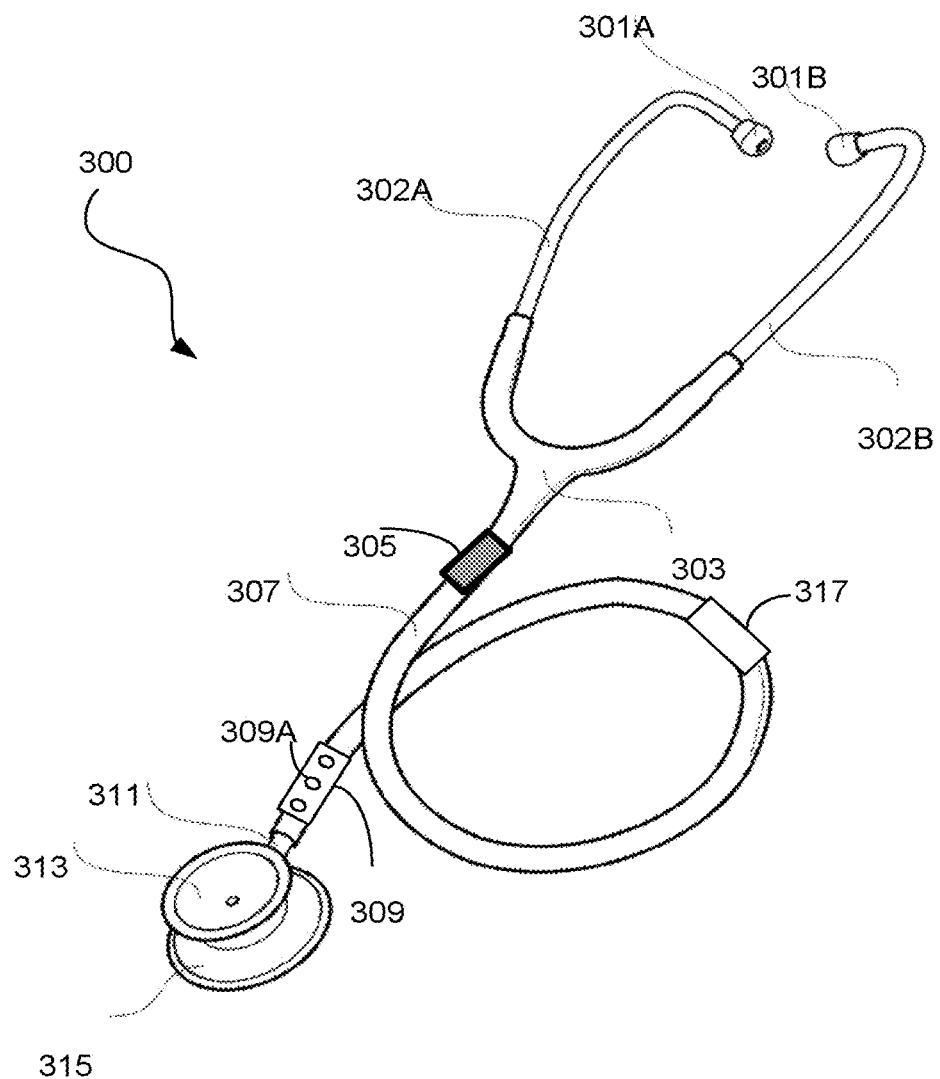
FIG. 3 illustrates an exemplary stethoscope according to an embodiment.

FIG. 3 illustrates an exemplary stethoscope 300 according to an embodiment of the present disclosure. The stethoscope 300 includes a sound receiving chest piece that may include both a bell 313 and an opposed diaphragm 315. According to one embodiment, the bell 313 and the diaphragm 315 may also be collectively referred to as the "chest piece." The bell 313 and diaphragm 315 are integrally-formed and connect by means of a tubular fitting 311 to a flexible tube 307, which includes a yoke 303.

Ear tubes 302A and 302B are connected to the tube 307 through the yoke 303 and include ear-tips 301A and 301B, which are received in the ears of the user. The frequencies detected and amplified by the bell 313 and/or the diaphragm 315 are transmitted through the tube 307 and the ear tubes 302A, 302B to the ear-tips 301A, 301B. The bell 313 and the diaphragm 315 comprise the patient-contacting portions of the stethoscope 300 and are the portions which should be covered and protected against contact with body fluids, tissue and skin.

Additionally, the stethoscope 300 includes a processor 305 and a light emitting diode (LED) panel 309 that includes a plurality of LED lights 309A. The stethoscope 300 also includes a display panel 317 that may be, for example, a liquid crystal display (LCD) panel, an organic electroluminescent (OLED) display panel, a plasma display panel, or the like. The display panel 317 may be used to display heart signals obtained from the bell 313 and the diaphragm 315 of the stethoscope 300.

According to one embodiment, the LED panel 309 includes a red LED, a green LED, and a yellow LED. The processor 305 includes sufficient memory having stored therein one or more sets of instructions, that is (are) executable by the processor 305, thereby enabling a user of the stethoscope 300 to successfully detect and distinguish Still's murmur from a pathological heart murmur. Specifically, the signals obtained from the bell 313 and the diaphragm 315 of the stethoscope may be processed by the processor 305, in order to diagnose the type of heart murmur in a patient. According to one embodiment, the LED panel 309 is used to provide a visual indication of the type of heart murmur detected. For instance, upon detecting Still's murmur in the patient, the stethoscope 300 may be configured to turn ON the yellow LED, whereas upon detecting a pathological murmur, the red LED may be activated. In the absence of any murmurs (i.e., a normal heart sound), the green LED may be activated. This allows the detected murmurs to be classified as either a pathological murmur or a Still's murmur. In other words, the apparatus and methods described in the present invention distinguish a Still's murmur from non-Still's murmurs (i.e., other innocent murmurs and pathological murmurs).

Figure 4:
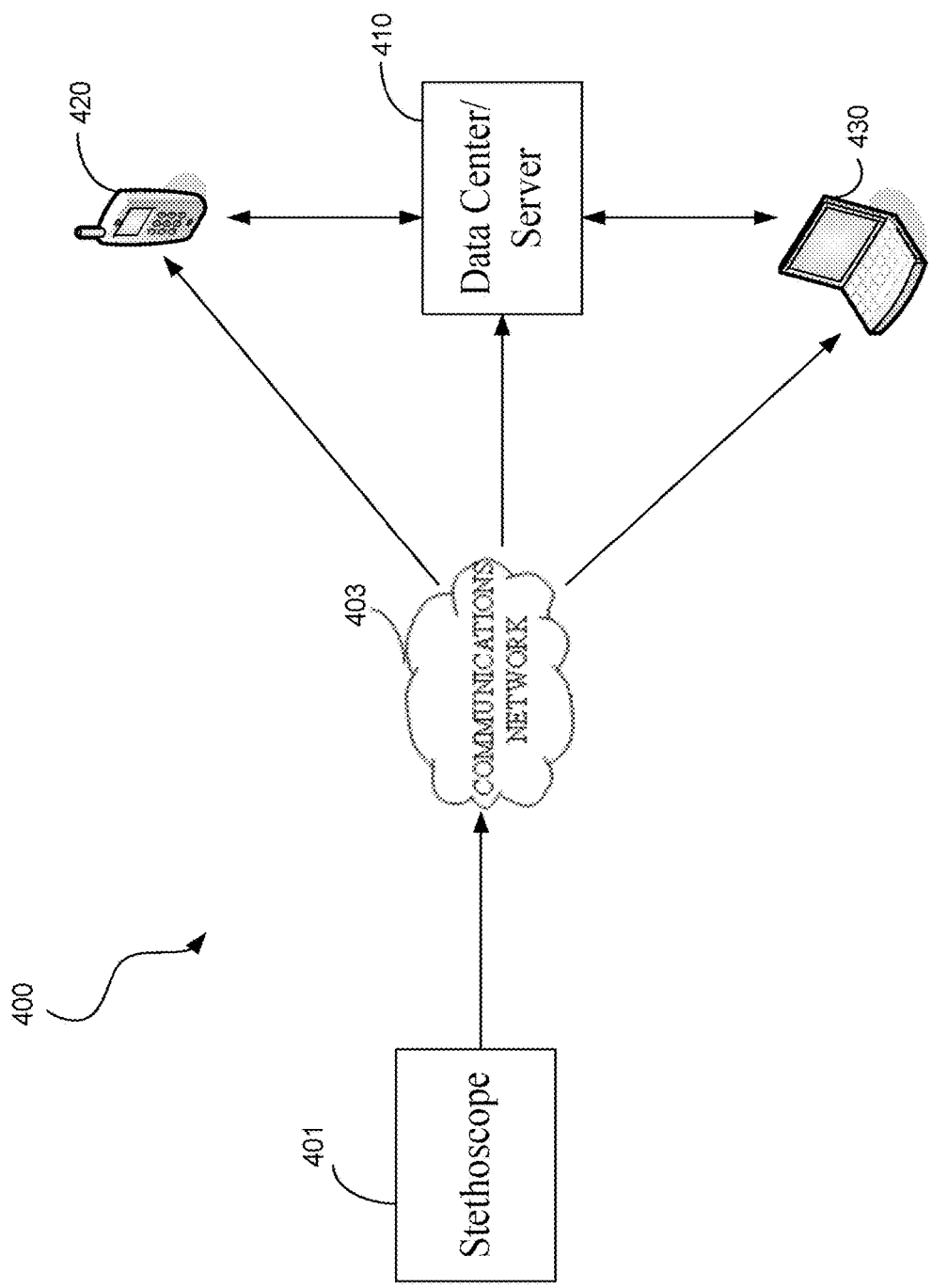
FIG. 4 illustrates, according to an embodiment, a schematic block diagram illustrating a stethoscope system.

FIG. 4 illustrates, according to an embodiment, a schematic block diagram illustrating a stethoscope system 400. The system 400 includes a stethoscope 401 that is configured to receive heart signals from a patient. The signals obtained by the stethoscope 401 may be processed either by a mobile device that is connected to the stethoscope 401 (as shown in FIGS. 1, 2A, and 2B), or alternatively, the heart signal may be processed by a processor (circuitry) that is built-in the stethoscope as shown in FIG. 3.

By one embodiment, the stethoscope 401 may communicate with a data center (server) 410 via a communications network 403. The stethoscope 401 may use transmission control protocol/Internet protocol (TCP/IP), user datagram protocol (UDP) or the like for transmission of medical information (patients' health record, heart signal, etc.) to the data center 410. Additionally, the data center 410 may include an applications server that is configured with web applications and client specific applications as needed for the organizing/maintaining and sharing of client information with medical professionals. In addition, the applications server may communicate with the communication network 403 via a router and be further protected and buffered by a firewall.

The stethoscope 401 may also be configured to transmit the detected heart signal to a mobile device 420 using the communication network 403. For instance, the stethoscope (via the communication network 403) may implement a packet switching approach such as connectionless packet switching (datagram switching) or a connection-oriented packet switching (virtual circuit switching) to transfer information to the mobile device 420. In a similar manner, the stethoscope 401 may also use the communication network 403 that may be a local area network (LAN) to transfer information to a workstation 430. Additionally, the workstation 430 may include a web-browser that facilitates communication with the application server included in the data center 410. Furthermore, the mobile device 420 may access the communication network 403, as well as communicate with the application server included in the data center 410 with a compatible web-browser or any user interface. In this manner, the data center 410 may provide client specific data upon demand.

It must be appreciated that additional and/or alternative configurations of the stethoscope system as described above are well within the scope of the present disclosure. For instance, in the case of the stethoscope having a built-in processor (processing circuitry) and a display panel as shown in FIG. 3, the stethoscope may communicate with the data center, workstation, and/or other mobile devices to receive medical information pertaining to a particular user.

Figure 5:
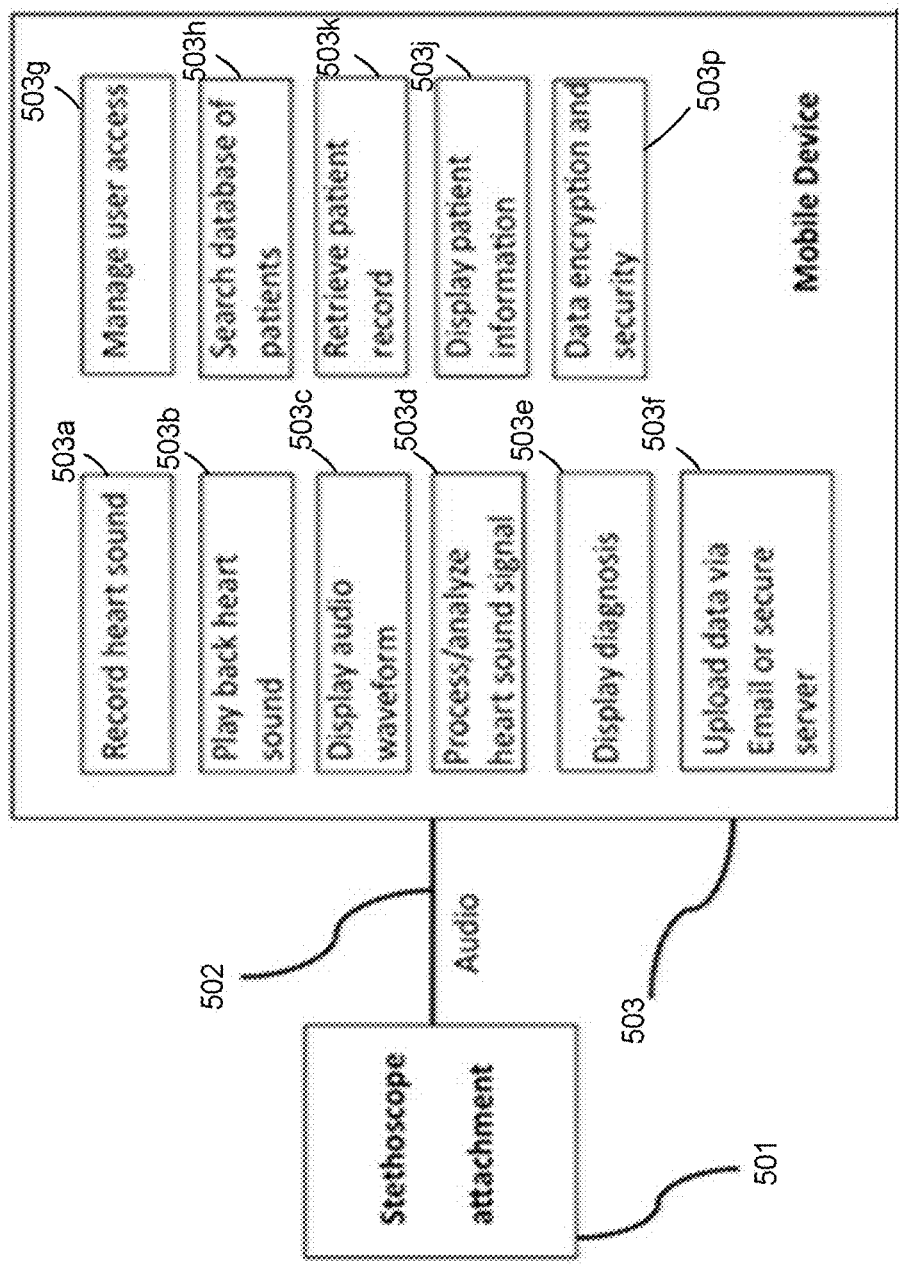
FIG. 5 depicts an exemplary block diagram illustrating functions performed by the mobile device.

FIG. 5 depicts an exemplary block diagram illustrating the functions performed by a mobile device pertaining to the heart sound (signal). Hereinafter the terms heart sound and heart signal are used synonymously and are implied to mean a signal obtained from the stethoscope placed on a patient's chest or other device that obtains heart signals.

According to an embodiment, a stethoscope may be attached via a stethoscope attachment 501 to the mobile device 503. Thus, the stethoscope can capture audio signals, for instance, heart murmur signals, and transfer the audio signal 502 to the mobile device 503 for further processing.

FIG. 5 depicts, according to an embodiment, applications that may be executed by the mobile device 503 in processing the heart signal that is transferred from the stethoscope. The hardware components of the mobile device 503 that execute the applications are described later with reference to FIG. 6. The applications can be accessed by a user via a user interface.

A heart sound captured by the mobile device may be recorded 503a and saved in memory of the mobile device 503 for further processing. Additionally, the heart signal stored in the memory of the mobile device may be retrieved by a processor (processing circuitry) of the mobile device to be played back 503b at a later time instant. Thus, in this manner, the mobile device can retrieve a previously stored heart signal of a patient and compare the stored heart signal with a current heart signal of the patient. The mobile device 503 is also configured to display a waveform 503c corresponding to the heart sound on a display panel of the mobile device.

By one embodiment, the mobile device processes (and analyzes) the heart signal 503d to determine whether the heart signal includes Still's murmur. Details regarding the processing performed by the mobile device to detect the presence of Still's murmur are described later with reference to FIGS. 10A, 10B, 11. Additionally, the mobile device 503 is also configured to display diagnostic information 503e pertaining to the processing of the heart signal. Such diagnostic information may be displayed on the display panel of the mobile device.

According to one embodiment, the mobile device 503 is also configured to perform communicative as well as organizational functions related to the heart signal. For instance, the mobile device may upload the heart signal 503f stored in the local memory of the mobile device to a remote server, for instance, via an email application, direct peer-to-peer communication with the server, via a cloud based application, and the like. The mobile device 503 may implement email protocols such as POP, IMAP and SMTP or the like, to email medical information of the user. Additionally, the mobile device 503 may use encryption techniques 503p such as hashing, symmetric cryptography, and asymmetric cryptography to transfer information from the mobile device 503 to the server and/or another mobile device.

Additionally, upon connecting with the remote server, the mobile device 503 may query the server to perform a search operation (for example, search a database of patients 503h) in order to retrieve information belonging to a particular user. In one embodiment, the remote server may have a dedicated database that stores patient information as individual records. The mobile device 503 may communicate with the remote server in order to retrieve a particular patient's medical information (record) 503k. Upon retrieving the patient's record, the mobile device 503 may display the record 503j on the display panel of the mobile device.

In one embodiment, each of the above stated functionalities may be performed by the mobile device 503 in the form of a user application or 'app', which is executable by the processor of the mobile device. Furthermore, the 'app' may also provide a way to create and manage user access 503g, by creating a secure account and preventing fraudulent attempts to access a user's record. Although applications 503a to 503p are described above, it should be noted that other applications commensurate with the scope of the description can be executed by the mobile device 503. For example, applications to review and edit the heart signals, to allow user entry of patient information via a user interface, to store information, to transmit information, and other related applications can be executed by the mobile device 503.

Figure 6:
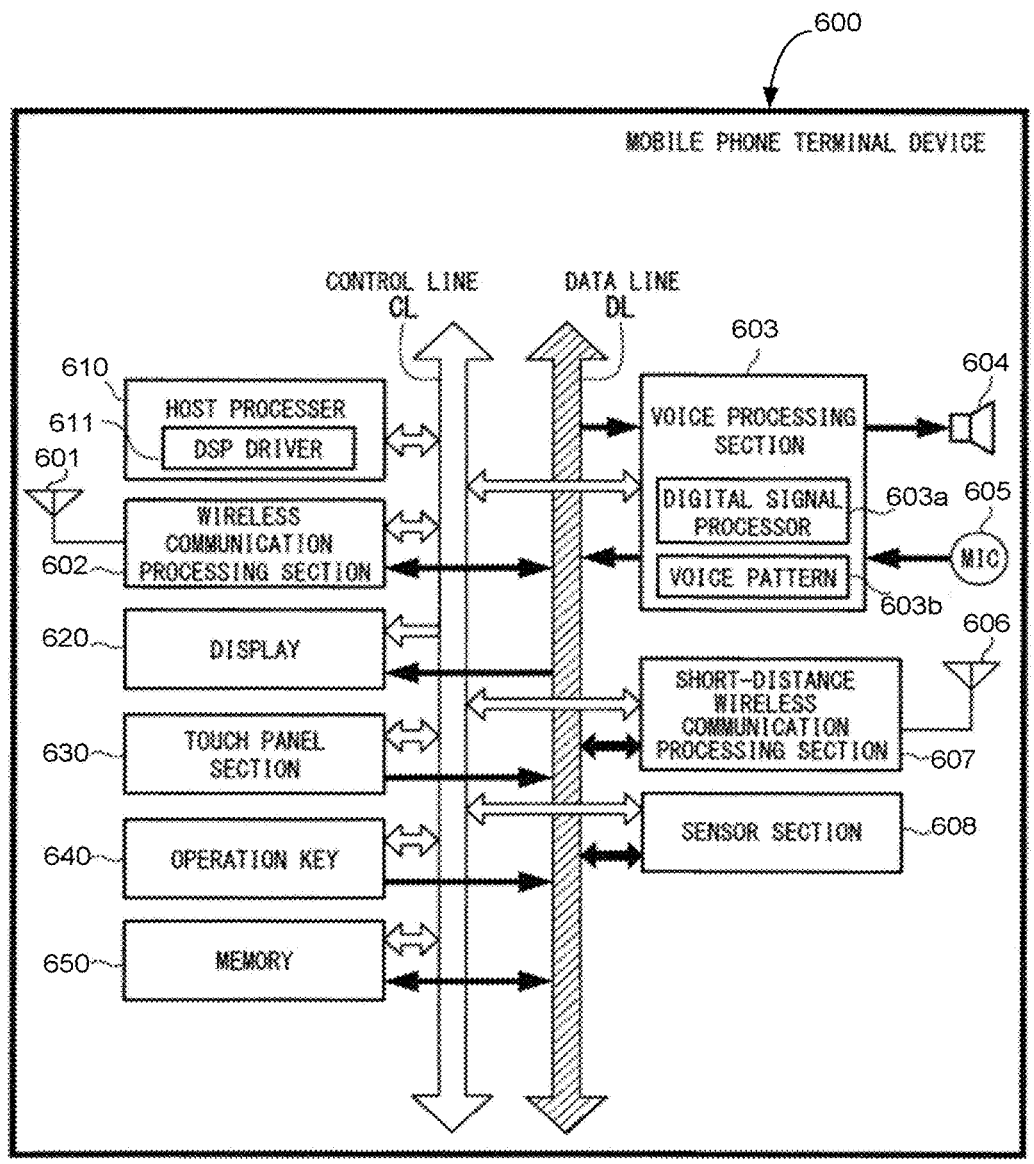
FIG. 6 illustrates schematically an exemplary mobile phone terminal device.

FIG. 6 illustrates a schematic block diagram of an exemplary mobile phone terminal device 600. The hardware components as depicted in FIG. 6 may be configured to perform the processing functions described with reference to FIG. 5. As shown in FIG. 6, the mobile phone terminal device 600 may include an antenna 601 and a wireless communication processing section 602. The wireless communication processing section 602 may communicate wirelessly via radio signals, or the like, with other mobile devices via a base station. Further, a data signal, such as a voice transmission from another user, may be received by antenna 601 and sent to the wireless communication processing section 602 for further processing. In the case of an incoming voice transmission, the voice data signal may be sent from the wireless communication processing section 602 to a voice processing section 603. Incoming voice data received by the voice processing section 603 via the wireless communication processing section 602 may be output as sound via a speaker 604.

Conversely, an outgoing voice signal may be supplied by a user to the voice processing section 603 via a microphone 605. The voice signal received via microphone 605 and processed by the voice processing section 603 may be sent to wireless communication processing section 602 for transmission by the antenna 601. The voice processing section 603 comprises a digital signal processor (DSP) 603a which digitizes the incoming analog signal and processes the audio input to detect for keywords. Keywords enable the operation of device 600, when it is configured to operate under the instructions of specific voice commands. These keywords are preset in the device with the aid of a voice registration unit and stored in the voice pattern library 603b.

A second antenna 606 may be supplied for use with a short distance wireless communication processing section 607. The short distance wireless communication processing section 607 may communicate wirelessly with other devices over a network, such as the Internet, a local area network (LAN), or a wide area network (WAN). The second antenna 606 may, e.g., by a Wi-Fi transceiver.

A sensor section 608 may be provided for the mobile phone terminal device 600. The sensor section 608 may be a motion sensor that detects a motion of an object in the proximity of the mobile phone terminal device 600. The motion may correspond to a user moving an instruction object, such as a finger or stylus, in the proximity of the mobile phone terminal device 600 for the purpose of selecting data displayed on display 620. The motion sensors may enable users to select a portion of a waveform (displayed on a display panel), e.g., a waveform corresponding to a heart murmur and further analyze/extract signal features from the selected signal portions.

The mobile phone terminal device 600 may include display 620. The display 620 may be, for example a liquid crystal display (LCD) panel, an organic electroluminescent (OLED) display panel, a plasma display panel, or the like. The display 620 may display text, an image, a web page, a video, or the like. For example, when the mobile phone terminal device 600 connects with the Internet, the display 620 may display text and/or image data which is transmitted from a web server in Hyper Text Markup Language (HTML) format and displayed via a web browser. The display 620 may additionally display data stored in a memory 650.

A touch panel section 630 can detect a touch operation on the surface of the display 620. For example the touch panel 630 can detect a touch operation performed by an instruction object such as a finger or stylus. Touch operations may correspond to user inputs such as a selection of an icon or a character string displayed on the display 620. The touch panel section 630 may be an electrostatic capacitance type device, a resistive type touch panel device, or other such type devices for detecting a touch on a display panel.

The touch panel section 630 may perform processing related to touch operation classification. For example, the touch panel section 630 may assign a predetermined function to be performed when a "tap" touch operation is detected. Similarly, the touch panel section may analyze a touch operation in which the instruction object makes continuous contact with the display 620 while moving the instruction object around the display 620 (e.g., a "swipe" operation). The touch panel section 630 may output a signal based on a classification of the touch operation performed. The signal may for example include information indicating the touch operation classification, the location on the display 620 where the touch operation was performed, and the operation to be performed based on the touch operation.

Data which is detected and processed by the touch panel 630 can be transmitted to a host controller 610. The host controller/processor 610 (processing circuitry) may include one or more processor units (circuits) and can control each element of the mobile phone terminal device 600 based on data detected by the touch panel 630, or by inputs received from operation key 640. The operation key 640 may receive inputs, e.g., from external control buttons included with the mobile phone terminal device 600. The external control buttons may for example control the volume, the power, or a hold operation for the mobile phone terminal device 600.

The host controller 610 may further execute instructions stored in the memory 650. The controller may further comprise of a DSP driver 611, which is configured to communicate with the DSP 603a. Specifically, the driver may actuate the DSP during a voice registering phase, or the DSP 603a may initiate communication with the driver upon the successful detection of a voice command. The driver 611 may further activate the host processor to execute a certain application based on the received voice commands. To this end, the memory 650 may be a non-transitory computer readable medium having instructions stored therein for controlling the mobile phone terminal device 600. Further, the controller 610 may include one or more processors for executing the instructions stored on the memory 650.

The mobile phone terminal device 600 can include a control line CL and a data line DL as internal bus lines for communication. The control line CL can be used to transmit control data from the controller 610. The data line DL may be used for the transmission of voice data, display data, or the like, throughout the various elements of the mobile phone terminal device 600.

Figure 7A:
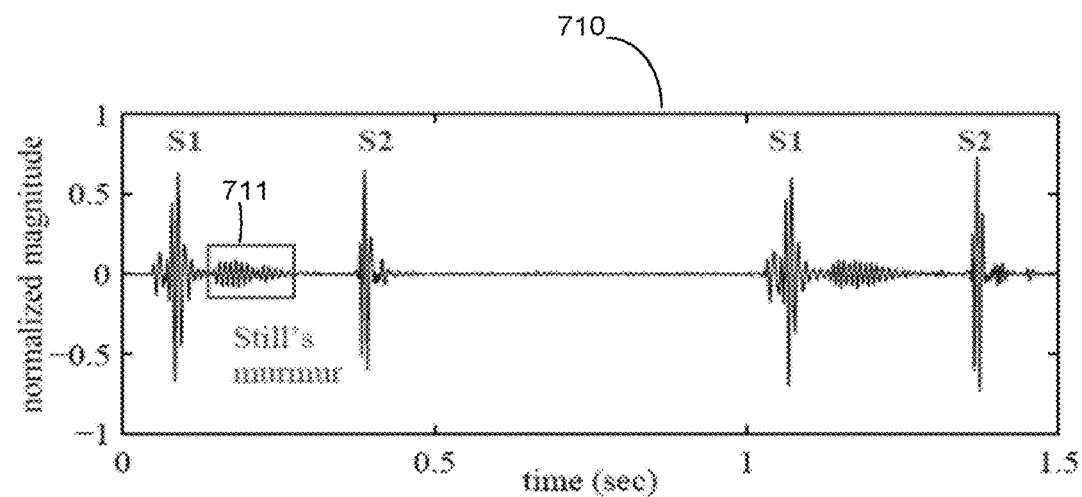
FIGS. 7A and 7B depict exemplary timing diagrams illustrating Still's and pathological murmurs, respectively.
Figure 7B:
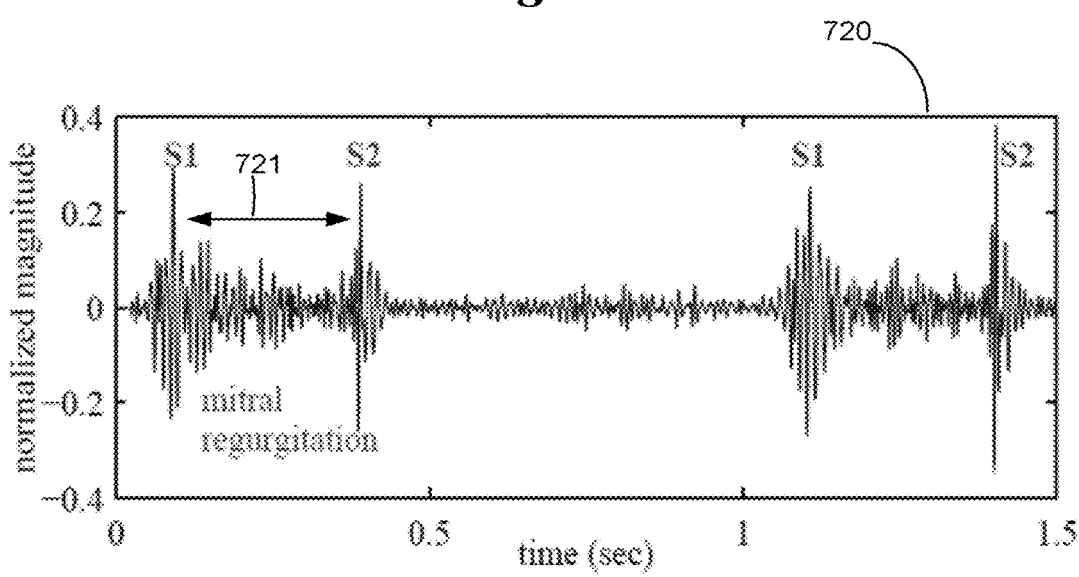

Turning to FIGS. 7A and 7B, there is depicted, according to an embodiment, exemplary timing diagrams illustrating Still's and pathological murmurs, respectively. FIG. 7A depicts a cardiac cycle 710 that includes the presence of a Still's murmur 711. Still's murmur is an early-to-mid-systolic low-pitched groaning murmur. As shown in FIG. 7A, the timing diagram is depicted with time being represented on the x-axis and a normalized magnitude of the murmur being represented on the y-axis. The Still's murmur 711 has a relatively pure tone and exists only for a short duration between a first heart sound lobe (S1) and a second heart sound lobe (S2) of the cardiac cycle 710.

FIG. 7B depicts a cardiac cycle 720 that includes a pathological murmur such as mitral regurgitation. In contrast to the Still's murmur of FIG. 7A, the pathological murmur has a longer duration and a higher magnitude. Specifically, the pathological murmur has a time duration 721 corresponding to the time interval between the first heart sound lobe (S1) and the second heart sound lobe (S2).

Figure 8:
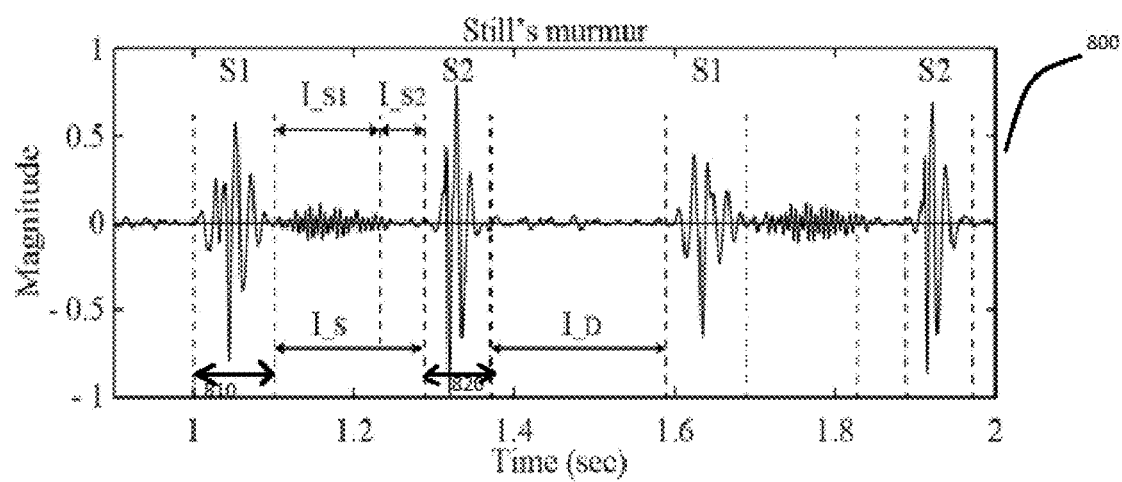
FIG. 8 depicts, according to an embodiment, an exemplary cardiac cycle including Still's murmur.

FIG. 8 depicts, according to an embodiment, an exemplary cardiac cycle 800 including a Still's murmur. The cardiac cycle 800 illustrates time intervals that correspond to the possible locations of Still's murmur and pathological systolic heart murmurs, respectively. The cardiac cycle 800 is depicted with time being represented on the x-axis and a normalized magnitude of the murmur being represented on the y-axis.

Specifically, the cardiac cycle 800 includes a first heart sound lobe S1, and a second heart sound lobe S2. The cardiac time interval 810 corresponds to the duration of the first heart sound and the cardiac interval 820 corresponds to the duration of the second heart sound. The time interval I_S corresponds to the systolic interval between S1 and S2 and the time interval I_D corresponds to the diastolic interval between S2 and S1. I_S includes I_S1 and I_S2. The time interval I_S1 (also referred to herein as $I_{Still}$) corresponds to the estimated location of Still's murmur. The time interval I_S2 is the time interval after I_S1. Still's murmur appears after S1 and an estimated location of the Still's murmur occurs within the time interval I_S1, which has a shorter duration than an interval between S1 and S2. By one embodiment, various cardiac cycles can be segmented (described later with reference to FIG. 9 and FIG. 11) in order to analyze the locations of S1, S2, and Still's murmur.

In one embodiment, upon analyzing 371 cardiac cycles of Still's murmur, it was observed that the time interval I_S1 was 70% of the systolic interval I_S.

Additionally, the cardiac cycle 800 depicts the possible location of other systolic heart murmurs. Specifically, the time interval I_S (referred to herein as $I_{non-Still}$) corresponds to the location of possible pathological murmurs. The interval I_S can be estimated based on the locations of S1 and S2 lobes. As described below with reference to FIG. 9, upon determining the locations of the S1 and S2 lobes of a cardiac cycle, various features can be extracted from the cardiac cycle in order to determine the presence of Still's murmur. For instance, in one embodiment, distinct features such as spectral width that represents the sharpness of a frequency response of the murmur, signal power that represents the signal intensity of the murmur, and shape (i.e. an envelope) of the murmur can be extracted from the cardiac cycle in order to distinguish between Still's murmur and a pathological murmur.

Figure 9:
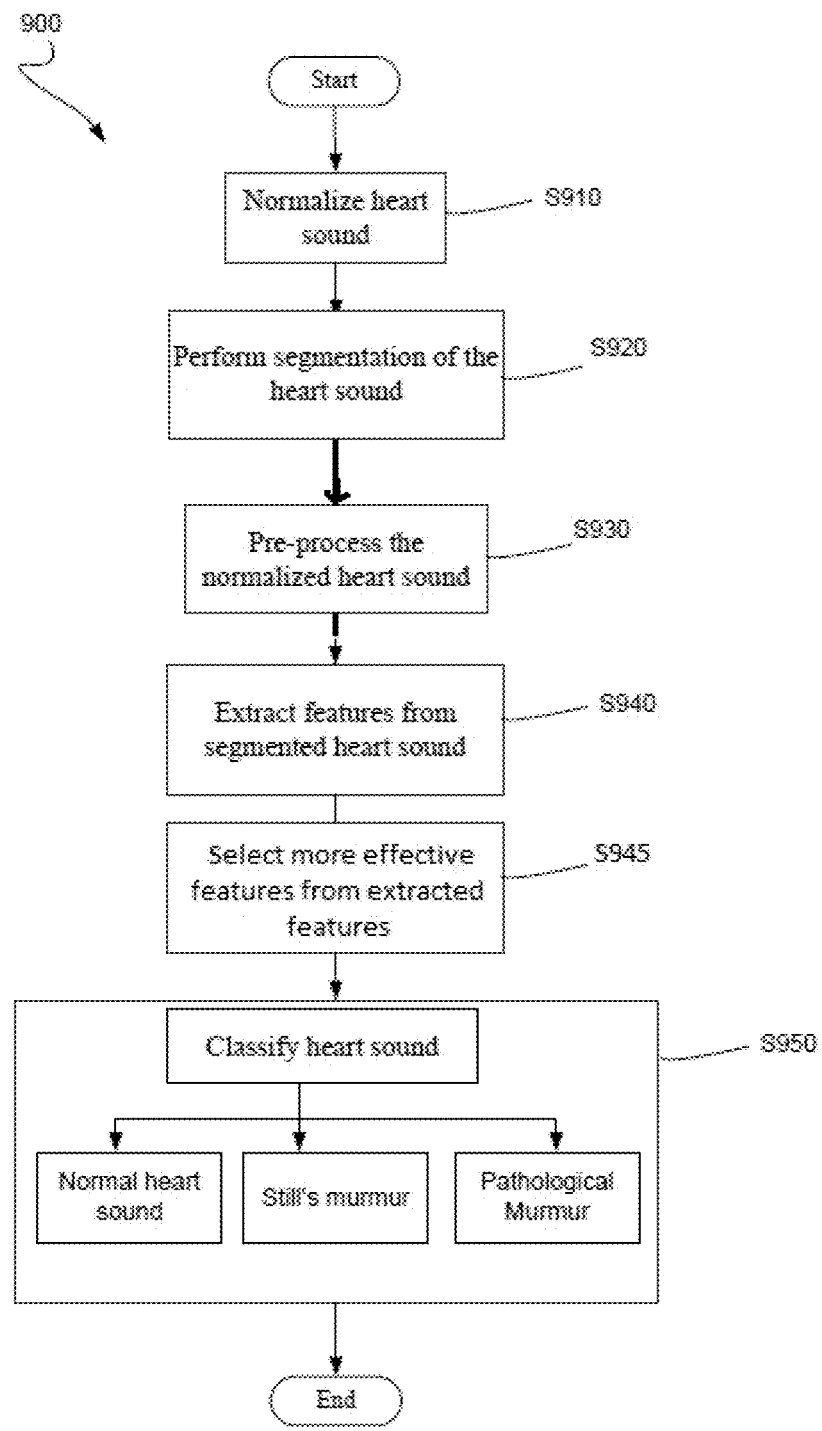
FIG. 9 illustrates, according to one embodiment, a flowchart depicting the steps performed to detect Still's murmur.

FIG. 9 illustrates, according to one embodiment, a flowchart 900 depicting the steps performed to detect Still's murmur. The steps of FIG. 9 may be performed for instance, by a mobile device that includes circuitry (e.g., host processor 610 of FIG. 6) configured to process a heart signal (heart sound) that is received from a stethoscope or may be performed in a server (or in a cloud) that includes circuitry and that is accessible to the mobile device.

In step S910, the process normalizes the received heart signal. Specifically, a normalization process is applied to the received heart signal that sets the amplitudes of the heart sound signal within ±1 range. The amplitude range of a heart sound can vary based on the recording conditions, location of the stethoscope on the chest, and the age and sex of the patient. Thus, the normalization process compensates for the patient-to-patient amplitude variations in the heart signal.

The process then proceeds to step S920 wherein the normalized heart sound of S910 is segmented. Specifically, a segmentation process is performed on the normalized heart signal in order to detect (i.e., locate and mark) S1 and S2 (see FIG. 8) of the heart signal. According to one embodiment, the segmentation may be performed based on the intensity and/or the energy of the heart signal. Furthermore, the segmentation may be performed manually or in an automated fashion (described later with reference to FIG. 11). Manual segmentation may be performed by using a GUI tool. Additionally, as described later with reference to FIG. 11, if the segmentation of the heart signal is performed in an automated manner, and the segmentation process fails to successfully segment the heart sound, this indicates the presence of pathological murmurs in the heart signal under consideration. Additionally, if the process determines that there are no murmurs in the heart signal, the process may classify the heart signal as a normal heart sound.

The process then proceeds to step S930, wherein the normalized heart signal is pre-processed. Specifically, the normalized heart signal is passed through a band-pass filter to eliminate the low and high frequency components that are not associated with heart murmurs. By one embodiment, the band-pass filter with a pass-band of 80 Hz-800 Hz is used. The passband may be selected based on the fact that the reported frequency range of most heart murmurs is approximately in the range of 110 Hz-786 Hz.

According to one embodiment, in order to determine the band-pass filter parameters, the filter order can be varied from 2 to 10 in steps of 1, the lower cutoff frequency can be varied from 50 Hz to 150 Hz in steps of 10 Hz, and upper cutoff frequency can be varied from 750 Hz to 830 Hz in steps of 10 Hz.

Further, the process in step S940 extracts features from the filtered, segmented heart signal, to determine whether the heart signal includes Still's murmur. According to one embodiment, 20 characteristic features based on location, signal intensities of signals in pre-defined intervals, a shape (a diamond crescendo/decrescendo envelope), and a frequency component are extracted and analyzed to determine the presence of Still's murmur.

According to one embodiment, average Shannon energies in intervals of S1, S2, I_S, I_D, and 4 evenly distributed intervals of I_S are measured. The average Shannon energy (Es) is defined as:

$$E_s = -\frac{1}{N} \cdot \sum_{i=1}^{N} x^2(i) \cdot \log x^2(i)$$

Where N is the number of samples in each interval and x is the pre-processed heart sound.

According to one embodiment, frequency characteristics of the heart signal are used to obtain information on pathological conditions. Autoregressive (AR) modeling and Fourier transform (FT) are used to estimate the power spectral density (PSD) of cardiac sounds. AR modeling assumes that the current value of a signal depends linearly on its previous values. AR modeling is used to predict future values and estimate the PSD of a signal. In one embodiment, the signal in the $I_{Still}$ period (i.e., period I_S1 in FIG. 8) of the cardiac cycle is denoted as X(n). Further, the edges of the truncated signal X(n) create a spectral leakage in the frequency domain. Thus, a Hanning window may be applied to reduce the spectral leakage before applying AR modeling. The AR model of order p is defined as:

$$X(n) = \sum_{k=1}^{p} a_k X(n-k) + e(n) \quad (1)$$

where $a_k$ are AR coefficients and e(n) is the prediction error. AR coefficients ($a_k$) can be estimated by minimizing the mean squared prediction error. Accordingly, the PSD estimate can be obtained as:

$$PSD(f) = \frac{T\sigma_w^2}{\left|1 + \sum_{k=1}^{p} a_k e^{-j2\pi fkT}\right|^2} \quad (2)$$

where $\sigma_w^2$ is the variance of a white noise input and T is the sampling period. In order to optimize the order of AR modeling, the order can be varied from 7 to 16. In one embodiment, an AR model of order 11 yields optimal results.

According to one embodiment, the spectral width and the peak frequency of the heart signal can be obtained from the estimated PSDs (from AR modeling and FT) of the signal in the $I_{Still}$ time period of the cardiac cycle. As stated previously, the Still's murmur has a low-pitched pure tone and is concentrated in a narrow frequency region, whereas the sounds of pathological murmurs are distributed widely with a higher peak frequency in the frequency domain. In one embodiment, upon estimating the PSD in the $I_{Still}$ time period (the possible location of Still's murmur), the spectral width for a predetermined reference threshold level and the peak frequency can be measured to determine the presence of Still's murmur.

Figure 10A:
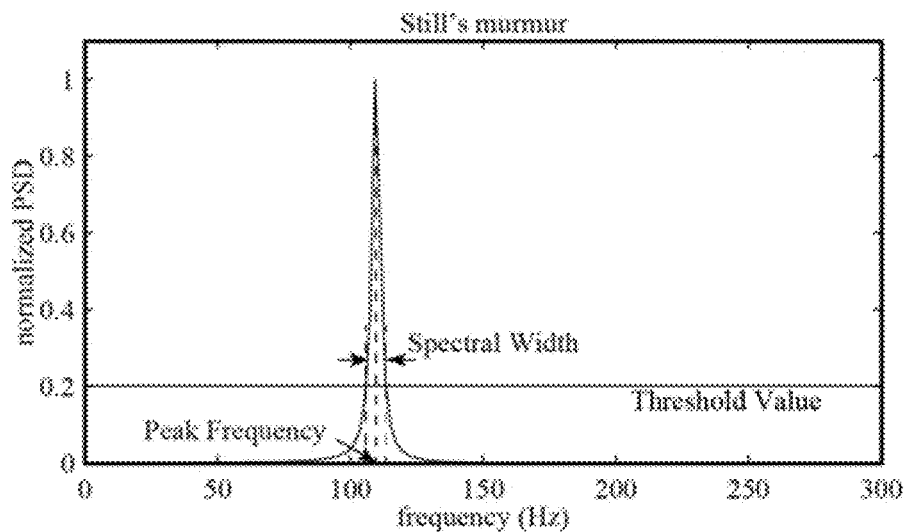
FIG. 10A and FIG. 10B illustrate exemplary power spectral densities of cardiac sounds.
Figure 10B:
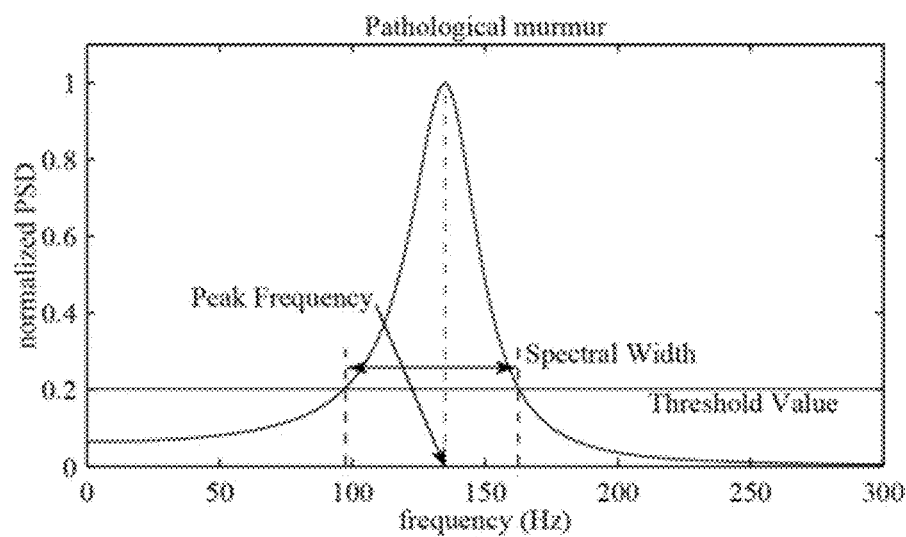

For instance, FIGS. 10A and 10B depict, according to an embodiment, exemplary spectral widths and peak frequencies (obtained from normalized PSDs using AR modeling) of Still's and pathological murmurs, respectively. Specifically, FIG. 10A depicts the normalized PSD (plotted on the y-axis) of Still's murmur, with the frequency being plotted on the x-axis. As shown in FIG. 10A, a threshold value, corresponding to 20% of the maximum PSD, is used to measure the spectral width. In other words, the spectral width is measured at a frequency where the magnitude of the PSD is 20% of the maximum PSD. The spectral widths and peak frequencies using FT are also measured with the same approach.

FIG. 10B depicts the normalized PSD (plotted on the y-axis), with frequency being plotted on the x-axis for a pathological murmur. As shown in FIG. 10B, for a 20% threshold value, the spectral width of a cardiac cycle that includes pathological murmurs is broadened. In other words, the spectral width of the cardiac cycle including pathological murmurs is significantly greater than the spectral width of a cardiac cycle that includes Still's murmur. FIG. 10B also shows that the peak frequency of pathological murmur is greater than the peak frequency of Still's murmur.

Figure 13A:
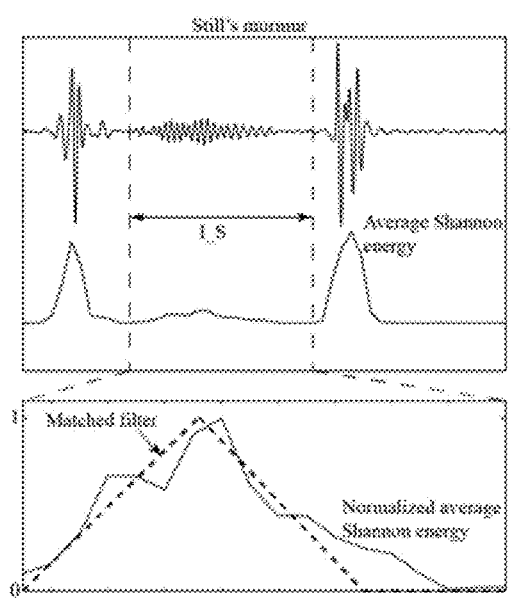
FIG. 13A and FIG. 13B illustrate an exemplary envelope of a matched filter.
Figure 13B:
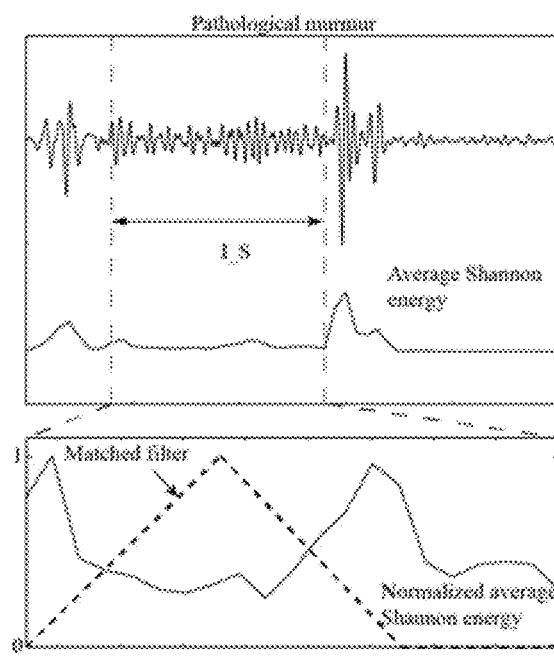

According to one embodiment, the distance between the matched filter that has an ideal envelop of Still's murmur and the normalized average Shannon energy of the interval I_S are illustrated in FIGS. 13A and 13B. FIGS. 13A and 13B show the envelope of the matched filter. The envelope of the matched filter increases until 50% of I_S1 ($I_{Still}$) and then decreases until the end of I_S1 (see FIG. 8 for illustration of I_S1). The average Shannon energy in I_S is normalized to set the maximum value to 1. In the case of Still's murmur, the distance between the matched filter and the normalized average Shannon energy in I_S is a smaller value than in the case of non-Still's murmurs.

According to one embodiment, the spectral widths using short time FT (STFT) in I_S are measured. The STFT over 50-ms sliding windows with 50% overlap is calculated. The spectral width in each sliding window is measured with a 20% reference threshold value. The mean, minimum, and maximum values of spectral widths in every sliding window are measured.

According to one embodiment, the spectral power in regions of 100 Hz-200 Hz and 200 Hz-500 Hz using STFT is measured. Generally, Still's murmur has a lower pitch than pathological murmurs. In each sliding window, PSDs corresponding to two frequency regions are added. The mean and maximum values of estimated powers in two regions are measured.

All extracted features are averaged over the measurements of every cycle.

Returning to FIG. 9, the process in step S945 selects more effective features from all extracted features for distinguishing Still's murmur from other murmurs. The best subset of extracted features is determined when the classification algorithm is trained and tested on the training set and test set. Sequential floating forward selection (SFFS) algorithm is used. SFFS starts with a null feature set. For each step, SFFS adds the best feature that satisfies the pre-defined criterion function in the current feature set. Then, it verifies the possibility of improvement of the criterion when the worst feature is removed. The number of features dynamically increases and decreases until the desired criterion is satisfied. In one embodiment, the criterion is the true positive rate (TPR) when the false positive rate (FPR) is 0% on the test set after training the classification algorithm on the training set. The true positive is the Still's murmur correctly detected by classifier and the false positive is the non-Still's murmurs incorrectly detected as Still's murmur. Other criterion and other feature selection methods can be used.

In step S950, in one embodiment, the process classifies the heart sound into three categories—normal heart sound, Still's murmur, and pathological murmur (or non-Still's murmur). The selected features are fed into a cascade classifier which is a Support Vector Machine (SVM). First, the heart sound is classified into a normal heart sound and murmur. If the heart sound is classified as a murmur, the second SVM decides whether the heart sound is Still's murmur or not. An artificial neural network (ANN) can be used for the classification method. ANN is trained using normal heart sounds, Still's murmur, and pathological murmurs (or non-Still's murmurs) and the ANN classifies the heart sound into a normal heart sound, Still's murmur, and pathological murmur (or non-Still's murmur). Additionally, the classifier such as SVM and ANN may classify the type of pathological murmurs. The classification of the heart sound into the above-noted three categories is based on comparisons made between a received heart signal and data (stored in a database) corresponding to definite clinical diagnosis of other heart signals that have been confirmed to include a Still's murmur, a non-Still's murmur, or a normal heart sound.

Figure 11:
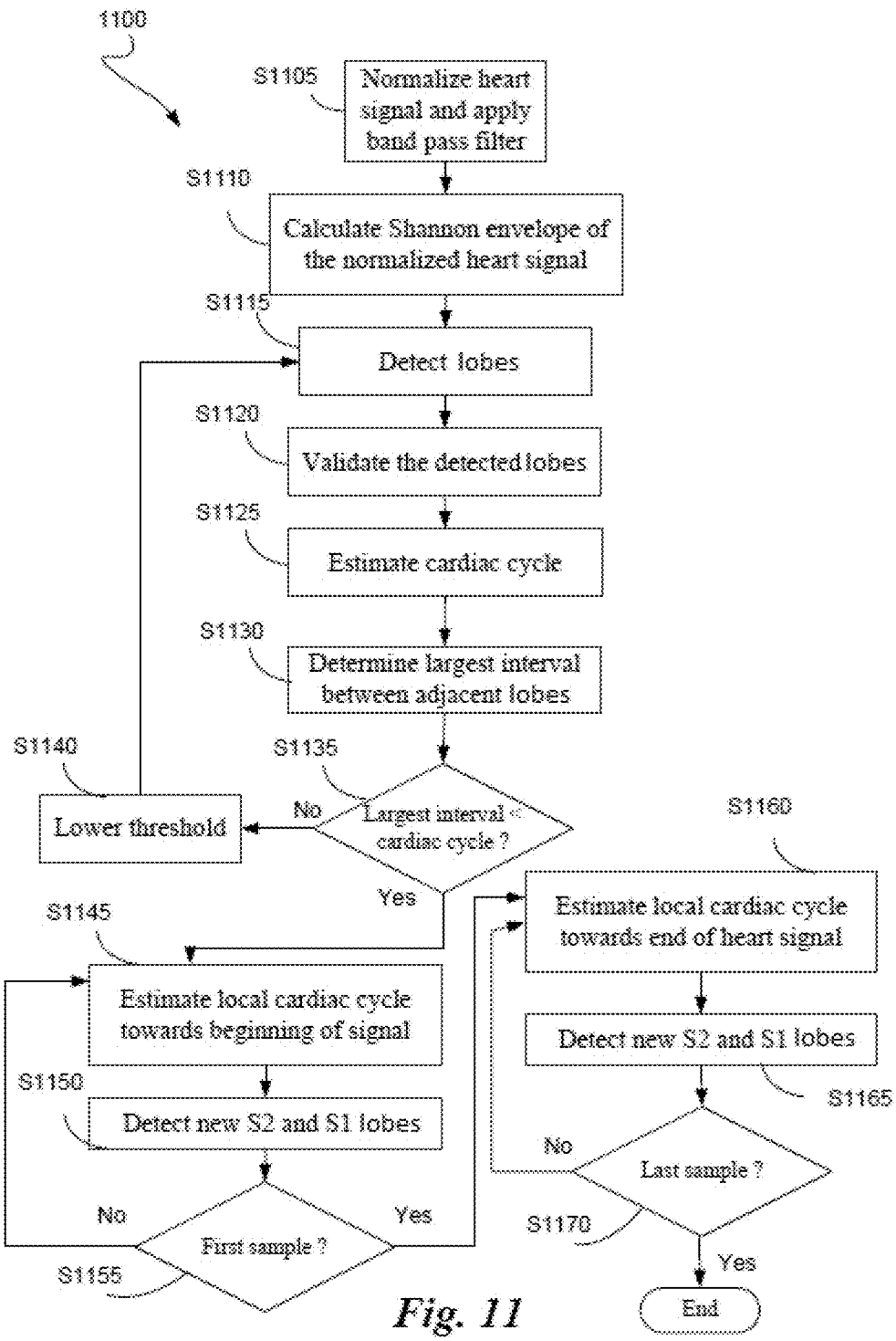
FIG. 11 illustrates an exemplary flowchart depicting the steps performed for automated heart signal segmentation.

FIG. 11 illustrates, according to an embodiment, an exemplary flowchart 1100 depicting the steps performed by an automated heart signal segmentation process. The automated heart signal segmentation process described herein is designed to detect S1 and S2 lobes of a heart signal. By one embodiment, the process is applied directly to the digitized heart sound captured for instance, from a stethoscope. If the automated heart sound segmentation fails, this indicates the potential presence of pathological murmurs.

The first step of the automated heart sound segmentation process is to identify significant sound lobes (S1, S2, other sound lobes) without any timing constraints. Further, the process screens detected sound lobes for S1 and S2 based on timing data. In recordings of normal heart sound, Still's murmur, and pathological murmurs, the automated heart sound segmentation process, as described below, produces reliable S1 and S2 segmentation with high accuracy. For instance, the automated segmentation process achieves a true positive rate of greater than 96.7%.

Turning to FIG. 11, in step S1105, the process normalizes the received heart signal. Specifically, a normalization process is applied to the received heart signal that sets the amplitudes of the heart sound signal within ±1 range. It must be appreciated that the amplitude range of a heart sound can vary based on the recording conditions, location of the stethoscope on the chest, and the age and sex of the patient. Thus, the normalization process compensates for the patient-to-patient amplitude variations in the heart signal. Furthermore, in step S1105, the normalized heart signal (sounds) are band-pass filtered to eliminate the low and high frequency components that are not associated with heart murmurs. By one embodiment, the band-pass filter with a passband of 40 HZ-500 Hz is used.

The process then proceeds to step S1110, wherein an average Shannon energy of the normalized and filtered heart signal is computed. The average Shannon energy is used to segment the heart signal. By one embodiment, the average Shannon energy is computed using a sliding window of 20 ms, with a 10 ms overlap. The Shannon energy of the envelope emphasizes on the medium intensity signal and attenuates the effect of low and high intensity signals.

The process then proceeds to step S1115, wherein sound lobes of the heart signal are detected. In one embodiment, the heart sound lobes are identified by applying a threshold value, for instance, an average value of the average Shannon energy over all of the time instants. Every portion of the heart signal (average Shannon energy) that is greater than the threshold value is identified as a sound lobe. Note that the detected sound lobe can be one of a S1 (first heart sound), a S2 (second heart sound), or other sounds.

Further, in step S1120, the detected heart sound lobes from step S1115 are validated based on their widths and a threshold distance (e.g., 50 ms) between adjacent sound lobes. In one embodiment, if the width of sound lobes is less than 250 ms, the sounds lobes are determined to be valid S1 and S2 candidates. However, if the distance between two consecutive sound lobes is less than 50 ms and the root mean square (RMS) energy of one sound lobe is less than a threshold value (e.g., 40% of the other's), splitting of sounds may occur. In this case, the sound with lower RMS is removed from further consideration.

Upon determining the S1 and S2 candidates, the process in step S1125 estimates the cardiac cycle of the heart signal. In one embodiment, the cardiac cycle is estimated based on an autocorrelation of the average Shannon energy. Further, the cardiac cycle is estimated at a time location corresponding to the time when the autocorrelation function has a maximum peak between 0.35 ms and 2 ms. Additionally, the initial estimation of the cardiac cycle may be used to validate the initial detection of S1 and S2 lobes.

Upon estimating the cardiac cycle, the process in step S1130 determines the largest interval between adjacent lobes. Specifically, a pair of S2 and S1 lobe is detected based on the assumption that the largest distance between two sound lobes occurs in the diastolic period of the cardiac cycle (i.e., the time period between an S2 lobe and the following S1 lobe, referred to herein as the S2-S1 time period). Generally, the diastolic period (i.e., the time period between an S2 lobe and the following S1 lobe, referred to herein as the S2-S1 time period is greater than the systolic period. Accordingly, the largest distance between two continuous sound lobes is selected, thereafter the first lobe of the two continuous selected lobes is marked as S2 and the second lobe is considered as S1.

The process then proceeds to step S1135, wherein a query is made to determine whether the largest interval between adjacent lobes, determined in step S1130, is less than the estimated length of the cardiac cycle (step S1125). If the response to the query is affirmative, the process proceeds to step S1145. However, if the response to the query is negative (i.e., the length of the largest interval is greater that the cardiac cycle), the process proceeds to step S1140. If the response to the query is negative, this indicates that the estimated cardiac cycle may be incorrect and/or there may be lobes within the heart signal that were not detected correctly due to a possibly high threshold value being used for sound lobe detection.

In step S1140, the threshold value (e.g., the average value of the average Shannon energy) used for detecting sound lobes of the heart signal is lowered, thereafter the process loops back to step S1115 and restarts the process of detecting the sound lobes of the heart signal.

Upon the query in step S1135 being affirmative, the process in FIG. 11 proceeds to step S1145, and in step S1150, new S1 and S2 lobes are detected that are disposed towards the beginning of the heart cycle (in reference to the position of the previously identified systolic period (S1-S2 time period) and S2). In the first iteration, only diastolic period (S2-S1 time period) with the largest distance is available. S2 and S1 are denoted with the largest distance as $S2_I$ and $S1_{I+1}$. To identify $S1_I$, possible candidates are searched for $S1_I$ within a pre-defined time window (i.e., the estimated cardiac cycle), and the correlation of the average Shannon energy between the possible systolic period (from the candidate to $S2_I$) and the next possible systolic interval (from the $S1_{I+1}$ and the time point that gives the same length of signal) is calculated. Different candidates have different systolic periods. The correlation measurements are normalized by the length of the systolic period, and the candidate with the maximum correlation is assigned as the true $S1_4$. After identifying $S1_I$, $S2_I$, and $S1_{I+1}$, a new $S1_{I-1}$ and $S2_{I-1}$ pair is detected using (1) the correlation between the average Shannon energy of the possible systolic period and that of the previously identified systolic period, (2) the estimated cardiac cycle length, and (3) the estimated systolic period. In one embodiment, the pre-defined time window (i.e., 2·Cycle) is used to find candidates for $S1_{I-1}$ and $S2_{I-1}$. If the number of candidates is less than 2, the search window can be increased. If the number of candidates is still less than 2, we assume that there is no S1 and S2 to be found. To identify the true $S1_{I-1}$ and $S2_{I-1}$ pair from the candidates, we compute three cost functions: (1) the correlation cost between the previous identified systolic envelope and the next possible systolic envelope (from $S1_{I-1}$ candidates to $S2_{I-1}$ candidates), (2) the difference between the previously defined cardiac cycle (the time period between $S1_I$ and $S1_{I+1}$) and the possible cardiac cycle (the time period between $S1_{I-1}$ candidate and $S1_I$), and (3) the difference between the previously defined systolic period (the time period between $S1_I$ and $S2_I$) and the possible systolic period (the time period between $S1_{I-1}$ candidate and $S2_{I-1}$ candidate). All three measurements are normalized to set the maximum score to 1 when there is no difference between previously identified S1-S2 pair and the candidate of S1-S2 pair. The total cost function is the summation of the three functions with weighting factors (i.e., 1:0.5:1). The weighting factor of 0.5 for the measurement of cardiac cycle is applied due to the high variation in the beat-to-beat interval of pediatric patients. The pair of candidates with the maximum score of the cost function is considered the true $S1_{I-1}$ and $S2_{I-1}$.

The process then proceeds to step S1155, wherein a query is made to determine whether the first peak sample that is disposed near the beginning of the cardiac cycle has been determined. Specifically, the query determines whether the processing of the beginning portion of the heart signal has been performed. If the response to the query is negative, the process loops back to step S1145 and repeats the detection of new pairs of S1 and S2 until the beginning of the heart signal is reached.

If the response to the query in step S1155 is affirmative, the process proceeds to step S1160. The processing performed in steps S1160, S1165, and S1170 are similar to the processing performed in steps S1145, S1150, and S1155, respectively, with the only difference being that the portion of the signal being processed in steps S1160, S1165, and S1170 lies to the right of the first identified $S2_I$ and $S1_{I+1}$ having the largest inter-peak distance. Specifically, the processing in steps S1160, S1165, and S1170 is performed in a direction that points towards the end of the heart signal using identified $S1_I$, $S2_I$, and $S1_{I+1}$. Upon detecting all the S1 and S2 lobes of the heart signal, the automated segmentation process of FIG. 11 terminates.

Figure 12:
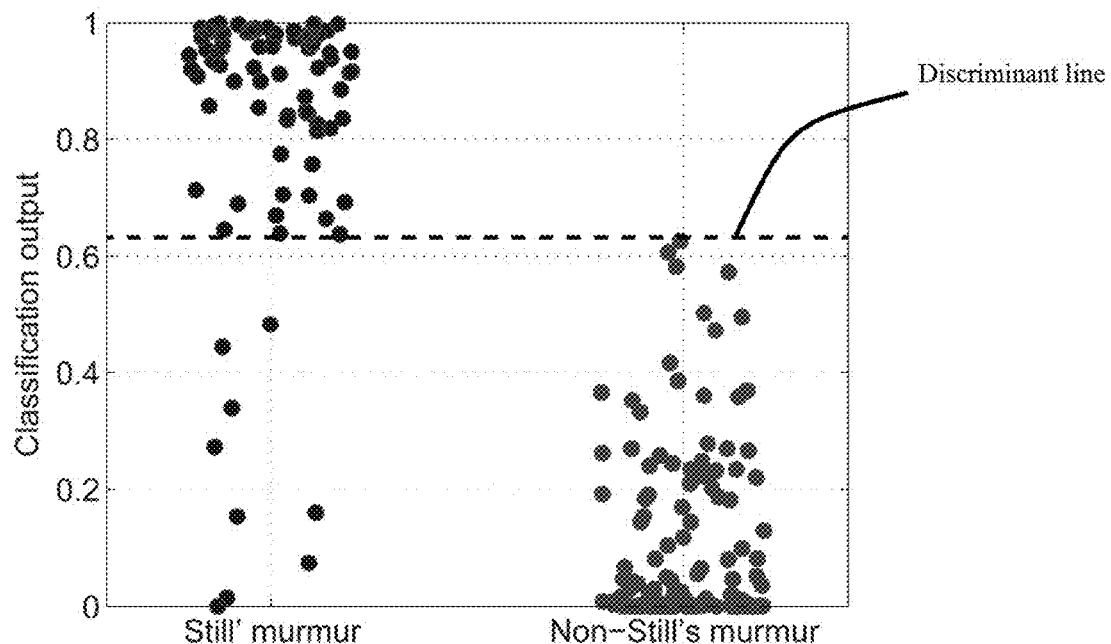
FIG. 12 illustrates, according to an embodiment, a graph representation of the classification result for Still's murmurs and non-Still's murmurs.

FIG. 12 illustrates, according to an embodiment, a graph representation of the classification result for 86 Still's murmurs and 116 non-Still's murmurs with confirmed diagnoses. The graph represents the output of SVM classifier with the selected features on the y-axis and with the type of murmurs on the x-axis.

In one embodiment, the 202 heart sound recordings (86 Still's and 116 pathological murmurs) with confirmed diagnoses are used to evaluate the method of FIG. 9. The heart sounds were recorded using a digital stethoscope (such as the 3M Littman Model 4100) and were digitized to 16 bits with a sampling frequency of 8000 Hz. Each digital recording includes 3-to-13 cardiac cycles. Jack-Knife method that is an iterative process in which data from one case is left out during training and used for validation of the network is used to evaluate the SVM classifier. The method Step 945 in FIG. 9 can be used to select more effective features to obtain the highest TPR when FPR is 0%. For example, for the discriminant line shown in FIG. 12, the TPR is 89.5% with 0% FPR. The threshold value to separate Still's murmur and non-Still's murmurs can be changed to adjust TPR and FPR.

In one embodiment, the method 900, as depicted in FIG. 9, can be used as a binary classifier to make a binary decision regarding the presence or absence of Still's murmur. In this case, the absence of Still's murmur can be classified as a non-Still's murmur without distinguishing between the different non-Still's murmurs. Note that an absence of murmur indicates a normal healthy heart. Accordingly, the binary classification system of the present embodiment counts true positives (defined herein as correctly detected Still's murmurs) and false positives (defined herein as incorrectly detected non-Still's murmurs).

Each of the functions of the described embodiments may be implemented by one or more processing circuits. A processing circuit or circuitry includes a programmed processor (for example, processor 1403 in FIG. 14), as a processor includes circuitry. A processing circuit also includes devices such as an application-specific integrated circuit (ASIC) and conventional circuit components arranged to perform the recited functions.

Figure 14:
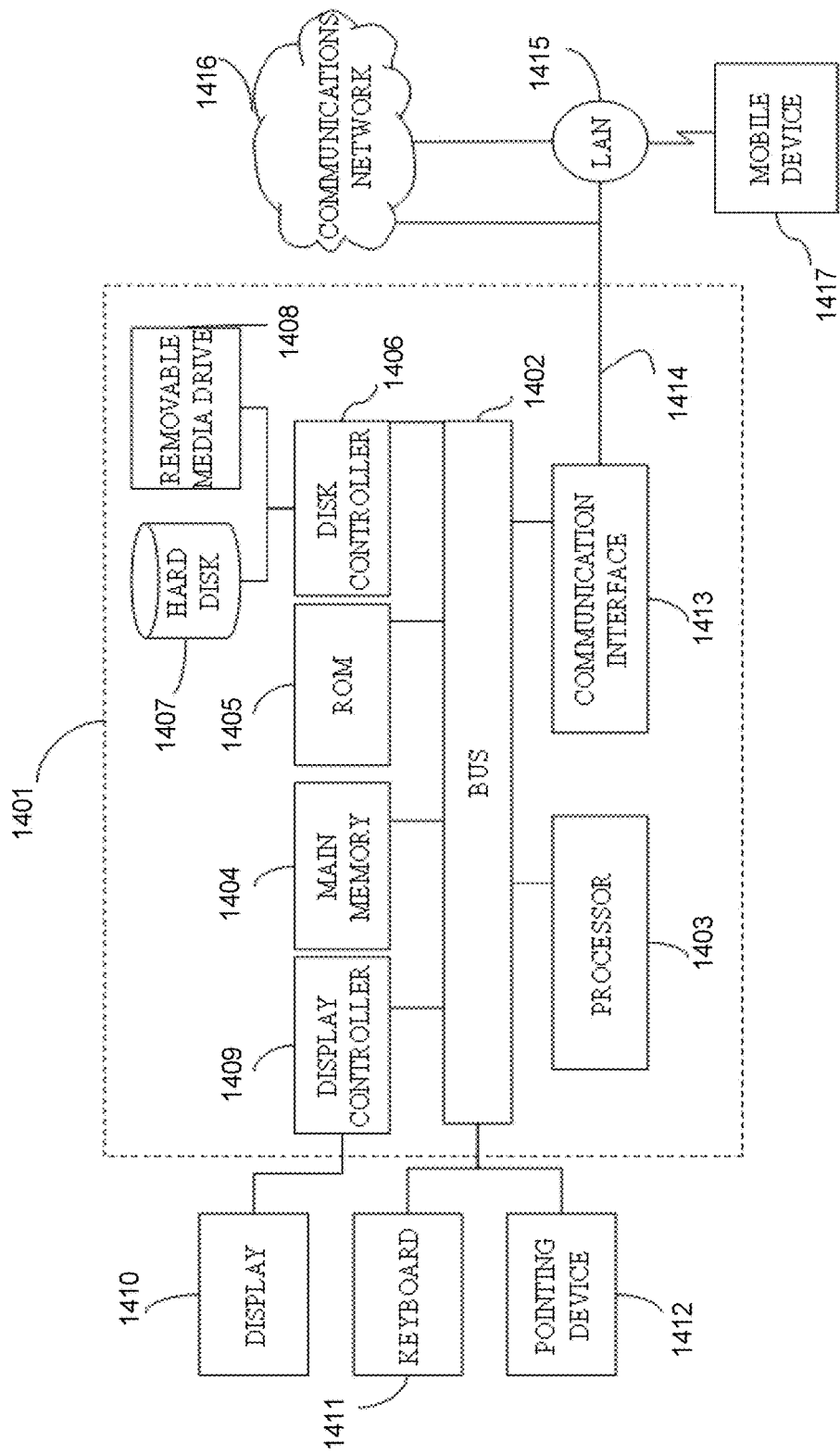
FIG. 14 illustrates a block diagram of a computing device according to one embodiment.

The various features discussed above may be implemented by a computer system (or programmable logic). FIG. 14 illustrates such a computer system 1401. Further, the computer system 1401 of FIG. 14 may be a special-purpose machine. In one embodiment, the computer system 1401 is a particular, special-purpose machine when the processor 1403 is programmed to process and analyze heart sounds in order to determine the presence of Still's murmur.

The computer system 1401 includes a disk controller 1406 coupled to the bus 1402 to control one or more non-transitory storage devices for storing information and instructions, such as a magnetic hard disk 1407, and a removable media drive 1408 (e.g., floppy disk drive, read-only compact disc drive, read/write compact disc drive, compact disc jukebox, tape drive, and removable magneto-optical drive). The storage devices may be added to the computer system 1401 using an appropriate device interface (e.g., small computer system interface (SCSI), integrated device electronics (IDE), enhanced-IDE (E-IDE), direct memory access (DMA), or ultra-DMA).

The computer system 1401 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1401 may also include a display controller 1409 coupled to the bus 1402 to control a display 1410, for displaying information to a computer user. The computer system includes input devices, such as a keyboard 1411 and a pointing device 1412, for interacting with a computer user and providing information to the processor 1403. The pointing device 1412, for example, may be a mouse, a trackball, a finger for a touch screen sensor, or a pointing stick for communicating direction information and command selections to the processor 1403 and for controlling cursor movement on the display 1410.

The processor 1403 executes one or more sequences of one or more instructions contained in a memory, such as the main memory 1404. Such instructions may be read into the main memory 1404 from another computer readable medium, such as a hard disk 1407 or a removable media drive 1408. One or more processors in a multi-processing arrangement may also be employed to execute the sequences of instructions contained in main memory 1404. In alternative embodiments, hard-wired circuitry may be used in place of or in combination with software instructions. Thus, embodiments are not limited to any specific combination of hardware circuitry and software.

As stated above, the computer system 1401 includes at least one computer readable medium or memory for holding instructions programmed according to any of the teachings of the present disclosure and for containing data structures, tables, records, or other data described herein. Examples of non-transitory computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium.

Stored on any one or on a combination of computer readable media, the present disclosure includes software for controlling the computer system 1401, for driving a device or devices for implementing the features of the present disclosure, and for enabling the computer system 1401 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 1403 for execution. A computer readable medium may take many forms, including but not limited to, non-volatile media or volatile media. Non-volatile media includes, for example, optical, magnetic disks, and magneto-optical disks, such as the hard disk 1407 or the removable media drive 1408. Volatile media includes dynamic memory, such as the main memory 1404. Transmission media, on the contrary, includes coaxial cables, copper wire and fiber optics, including the wires that make up the bus 1402. Transmission media also may also take the form of acoustic or light waves, such as those generated during radio wave and infrared data communications.

Various forms of computer readable media may be involved in carrying out one or more sequences of one or more instructions to processor 1403 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 1401 may receive the data on the telephone line and place the data on the bus 1402. The bus 1402 carries the data to the main memory 1404, from which the processor 1403 retrieves and executes the instructions. The instructions received by the main memory 1404 may optionally be stored on storage device 1407 or 1408 either before or after execution by processor 1403.

The computer system 1401 also includes a communication interface 1413 coupled to the bus 1402. The communication interface 1413 provides a two-way data communication coupling to a network link 1414 that is connected to, for example, a local area network (LAN) 1415, or to another communications network 1416 such as the Internet. For example, the communication interface 1413 may be a network interface card to attach to any packet switched LAN. As another example, the communication interface 1413 may be an integrated services digital network (ISDN) card. Wireless links may also be implemented. In any such implementation, the communication interface 1413 sends and receives electrical, electromagnetic or optical signals that carry digital data streams representing various types of information.

The network link 1414 typically provides data communication through one or more networks to other data devices. For example, the network link 1414 may provide a connection to another computer through a local network 1415 (e.g., a LAN) or through equipment operated by a service provider, which provides communication services through a communications network 1416. The local network 1414 and the communications network 1416 use, for example, electrical, electromagnetic, or optical signals that carry digital data streams, and the associated physical layer (e.g., CAT 5 cable, coaxial cable, optical fiber, etc.). The signals through the various networks and the signals on the network link 1414 and through the communication interface 1413, which carry the digital data to and from the computer system 1401 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1401 can transmit and receive data, including program code, through the network(s) 1415 and 1416, the network link 1414 and the communication interface 1413. Moreover, the network link 1414 may provide a connection through a LAN 1415 to a mobile device 1417 such as a personal digital assistant (PDA) laptop computer, or cellular telephone.

While aspects of the present disclosure have been described in conjunction with the specific embodiments thereof that are proposed as examples, alternatives, modifications, and variations to the examples may be made. Furthermore, the above disclosure also encompasses the embodiments noted below. It should be noted that, as used in the specification and the appended claims, the singular forms "a," "an," and "the" include plural referents unless the context clearly dictates otherwise.

The invention claimed is:

1. A system comprising: a device including an input port configured to receive a heart signal from a stethoscope;
   a connector that connects the device to the stethoscope and configured to relay the heart signal from the stethoscope to the device; and
   circuitry configured to classify an extracted feature of the heart signal as a Still's murmur after processing the heart signal,
   wherein the circuitry is configured to classify the extracted feature of the heart signal as the Still's murmur after processing the heart signal by being configured to:
   segment the heart signal to detect a first lobe (S1) and a second lobe (S2) of the heart signal,
   compute a spectral width of the extracted feature that lies in a portion of a time interval between the S1 lobe and the S2 lobe based on an estimated power spectral density,
   compute a peak frequency of the extracted feature of the heart signal,
   compute a shape of an envelope of the extracted feature of the heart signal, and
   classify the extracted feature of the heart signal as the Still's murmur based on the spectral width, the peak frequency, and the shape of the envelop.

2. The system according to claim 1, wherein the input port of the device is one of an audio port or a data port.

3. The system according to claim 1, wherein
   the connector includes a mount that is affixed to the device,
   an external contour of the mount matches a contour of the device, and
   the mount includes an attachment that connects to a stethoscope attachment and through which the heart signal is received.

4. The system according to claim 1, wherein
   the connector includes a microphone attachment, a cable, and a microphone receiver,
   the microphone attachment connects to the input port of the device,
   the microphone receiver connects to an input port of the stethoscope, and
   the cable connects the microphone attachment to the microphone receiver.

5. The system according to claim 1, wherein
   the connector includes a cable, an attachment, and a microphone receiver,
   the attachment includes an analog-to-digital converter and a pre-amplifier,
   the microphone receiver receives an analog heart signal from the stethoscope,
   the analog-to-digital converter converts the analog heart signal into a digital heart signal, and
   the cable relays the digital heart signal to the input port of the device.

6. The system according to claim 1, wherein the circuitry is configured to classify the extracted feature as the Still's murmur based on whether the spectral width is within a predetermined threshold.

7. A device comprising:
   an input port configured to receive a heart signal;
   a display configured to display the heart signal, to display a user interface to allow a user to review and edit the heart signal, and to display sound corresponding to the heart signal; and
   circuitry configured to classify an extracted feature of the heart signal as a Still's murmur after processing the heart signal,
   wherein the circuitry is configured to classify the extracted feature of the heart signal as the Still's murmur after processing the heart signal by being configured to:
   segment the heart signal to detect a first lobe (S1) and a second lobe (S2) of the heart signal,
   compute a spectral width of the extracted feature that lies in a portion of a time interval between the S1 lobe and the S2 lobe based on an estimated power spectral density,
   compute a peak frequency of the extracted feature of the heart signal,
   compute a shape of an envelope of the extracted feature of the heart signal, and
   classify the extracted feature of the heart signal as the Still's murmur based on the spectral width, the peak frequency, and the shape of the envelop.

8. The device according to claim 7, wherein the user inputs patient data information via the user interface, and the device further comprising:
   a memory configured to store the patient data information, the heart signal, the sound corresponding to the heart signal, and the edited heart signal.

* * * * *